(12) United States Patent
Fang et al.

(10) Patent No.: US 8,247,195 B2
(45) Date of Patent: Aug. 21, 2012

(54) METHODS AND HOST CELLS FOR RECOMBINANT PROTEIN EXPRESSION

(75) Inventors: Ferric C. Fang, Mercer Island, WA (US); William Wiley Navarre, Toronto (CA); Stephen J. Libby, Issaquah, WA (US)

(73) Assignee: The University of Washington, Seattle, WA (US)

( * ) Notice: Subject to any disclaimer, the term of this patent is extended or adjusted under 35 U.S.C. 154(b) by 562 days.

(21) Appl. No.: 12/015,443

(22) Filed: Jan. 16, 2008

(65) Prior Publication Data

US 2008/0299617 A1 Dec. 4, 2008

Related U.S. Application Data

(60) Provisional application No. 60/885,198, filed on Jan. 16, 2007.

(51) Int. Cl.
*C12P 21/04* (2006.01)
*C12N 1/20* (2006.01)

(52) U.S. Cl. .................. 435/69.6; 435/252.33; 435/69.1

(58) Field of Classification Search ........................ None
See application file for complete search history.

(56) References Cited

U.S. PATENT DOCUMENTS

| | | | |
|---|---|---|---|
| 4,683,202 | A | 7/1987 | Mullis |
| 6,190,867 | B1 | 2/2001 | Summers et al. |

OTHER PUBLICATIONS

Mizuno et al, (Function of the *Escherichia coli* nucleoid protein, H-NS: molecular analysis of a subset of proteins whose expression is enhanced in an hns deletion mutant. Mol. Gen. Genet. Feb. 1993; 237(1-2):113-22).*
Wyborn et al. (Regulation of *Escherichia coli* Hemolysin E Expression by H-NS and *Salmonella* SlyA ) Journal of Bacteriology, 2004, p. 1620-1628, vol. 186, No. 6.*
Paytubi et al (YdgT, the Hha paralogue in *Escherichia coli*, forms heteromeric complexes with H-NS and StpA. Molecular Microbiology (2004) vol. 54, Issue: 1, pp. 251-263).*
Williams et al. Probing the structure, function and interaction of the *E. coli* H-NS and StpA proteins by using dominant negative derivatives p. 4335-4343 J. Bac. 1996).*
Navarre et al Selective silencing of Foreign DNA with low GC content by the HNS protein in *Salmonella*. Published Online Jun. 8, 2006 Science Jul. 14, 2006: vol. 313 No. 5784 pp. 236-238.*
Altschul et al., Basic Local Alignment Search Tool; 1990, *Journal of Molecular. Biology*, 215:403410, pp. 403-410.
Amann et al., Vectors bearing a hybrid *trp-lac* promoter useful for regulated expression of cloned genes in *Escherichia coli*, Gene 25:167-178, 1983.
Arnheim and Levinson, Polymerase Chain Reaction, Chemical & Engineering News 36-47, 1990.
Barringer et al., Blunt-End and single-strand ligation by *Escherichia coli* ligase: influence on an in vitro amplification scheme; Gene 89: 117-122, 1990.
Barth et al., Role for the Histone-Like Protein H-NS in Growth Phase-Dependent and Osmotic Regulation of $\sigma^s$ and Many $\sigma^s$-Dependent Genes in *Escherichia coli*, Journal of Bacteriology 177: 3455-3464, 1995.
Beltrametti et al., Transcriptional Regulation of the *esp* Genes of Enterhemorrhagic *Escherichia coli*, Journal of Bacteriology 181: 3409-3418, 1999.
Berger and Kimmel, Guide to Molecular Cloning Techniques, Methods in Enzymolog vol. 152, Sections III and IV, Academic Press, Inc., San Diego, Calif, 1997.
Brunetti et al., The looped domain organization of the nucleoid in histone-like protein defective *Escherichia coli* stains; Biochimie 83: 873-882, 2001.
Brutlag et al., Improved Sensitivity of Biological Sequence Database Searches; 1990 Computer Application in the Biosciences; 6:237-245.
Bustamante et al., Transcriptional Regulation of type III Secretion Genes in Enteropathopenic *Escherichia coli*: Ler Antagonizes H-NS-Dependent Repression; Molecular Microbiology 39: 664-678, 2001.
Coker, Christopher et al., H-NS is a Repressor of the *Proteus mirabilis* Urease Transcriptional Activator Gene ureR; Journal of Bacteriology 182: 2649-2653, 2000.
Datsenko and Wanner, One-step inactivation of chromosomal genes in *Escherichia coli* K-12 using PCR products; Proc Natl Acad Sci U S A 97: 6640-5, 2000.
de Boer et al., The *tac* promoter: A function hybrid derived from the *trp* and *lac* promoters; Proc. Natl. Acad. Sci. USA 80: 21-25, 1983.
Dorman, Charle J.; H-NS: A Universal regulator for a Dynamic Genome; Nature Reviews Microbiology 2: 391-400, 2004.
Forsman et al., Antirepression function in *Escherichia coli* for the cAMP-cAMP receptor protein transcriptional activator; Proc Natl Acad Sci USA 89: 9880-9884, 1992.
Free, Andrew et al., The StpA Protein Functions as a Molecular Adapter to Mediate Respression of the *bgl* Operon by Truncated H-NS in *Escherichia coli*; Journal of Bacteriology 180: 994-997, 1998.
Gish, Warren and States, David J.; Identification of protein coding regions by database similarity search; 1993, Nature Genetics, 3:266-272.
Goeddel et al., Synthesis of human fibroblast interferon by *E. coli*; Nucleic Acids Res. 8: 4057-4074, 1980.
Guatelli et al., Isothermal, in vitro amplification of nucleic acids by a multienzyme reaction modeled after retroviral replication; Proc. Natl. Acad. Sci. USA 87: 1874-1878, 1990.
Haack et al., Interaction of Ler at the *LEE5* (tir) Operon of Enteropathogenic *Escherichia coli*; Infection and Immunity 71: 384-392, 2003.
Hardy and Cozzarelli; A genetic selection for supercoiling mutants of *Escherichia coli* reveals proteins implicated in chromosome structure; Molecular Microbiology 57: 1636-1652, 2005.
Heroven et al.; RovA is autoregulated and antagonizes H-NS-mediated silencing of invasion and *rovA* expression in *Yersinia pseudotuberculosis*; Molecular Microbiology 53: 871-888, 2004.

(Continued)

*Primary Examiner* — Kagnew H Gebreyesus
(74) *Attorney, Agent, or Firm* — Nixon Peabody LLP

(57) ABSTRACT

Methods for expressing recombinant polypeptides in host cells and host cells for polypeptide expression are provided.

28 Claims, 15 Drawing Sheets

OTHER PUBLICATIONS

Higgins et al.; Using Clustal for Multiple Sequence Alignments; 1996, Meth. Enzymol. 266:383-402.

Krishnan et al.; Effect of Anaerobiosis on Expression of Virulence Factors in *Vibrio cholerar*; Infection and Immunity 72: 3961-3967, 2004.

Kwoh et al.; Transcription-based amplification system and detection of amplified human immunodeficiency virus type 1 with a bead-based sandwich hybridization format; Proc. Natl. Acad. Sci. USA 86: 1173-1177, 1989.

Landegren et al., A Ligase-Mediate Gene Detection Technique; Science 241: 1077-1080, 1988.

Lee et al.; Genomic Conflict Settled in Favour of the Species Rather Than the Gene at Extreme GC Percentage Values; Appl Bioinformatics 3: 219-228, 2004.

Lomell et al.; Quantitative Asays Based on the Use of Replicatable Hybridization Probes; J. Clinical Chemistry; 35: 1826-1831, 1989.

Nasser and Reverchon, H-NS-dependent activation of pectate lyases synthesis in the phytopathogenic bacterium *Erwinia chrysanthemi* is mediated by the PecT repressor; Molecular Microbiology 43: 733-748, 2002.

Nieto et al. Evidence for Direct Protein-Protein Interaction between Members of the Enterobacterial Hha/YmoA and H-NS Families of Protein; Journal of Bacteriology 184: 629-635, 2002.

Paytubi et al.; YdgT, The Hha paralogue in *Escherichia coli*, forms heteromeric complexes with H-NS and StpA; Molecular Microbiology 54: 251-263, 2004.

Innis et al eds; PCR Protocols a Guide to Methods and Applications Academic Press Inc. San Diego, Calif. pp. 1-91, (1990).

Pearson and Lipman, Improved tools for biological sequence comparison; 1988, Proc. Natl. Acad. Sci. USA, 85:2444-2448.

Porwollik et al.; Characterization of *Salmonella enterica* Subspecies I Genovars by Use of Microarrays; Journal of Bacteriology 186: 5883-98, 2004.

Rowe and Summers; The Quiescent-Cell Expression System for Protein Synthesis in *Escherichia coli*; Applied and Environmental Microbiology 65: 2710-2715, 1999.

Sharpe et al.; Analysis of the ColE1 stability determinant Rcd; Microbiology 145:2135-44, 1999.

Shimatake et al.; Purified λ regulatory protein cII positively activates promoters for lysogenic development; Nature 292: 128-132, 1981.

Takeshita et al.; High-copy-number and low-copy-number plasmid vectors for *lacZa*-complementation and chloramphenicol- or kanamycin-resistance selection; Gene 61: 63-74, 1987.

Tendeng and Bertin; H-NS in Gram-negative bacteria: a family of multifaceted proteins; Trends in Microbiology 11(11): 511-518, 2003.

Thompson et al., Clustal W: improving the sensitivity of progressive multiple sequence alignment through sequence weighting, position-specific gap penalties and weight matrix choice; 1994, Nucleic Acids Research., 22:4673-4680.

Tupper et al.; The chromatin-associated protein H-NS alters DNA topology in vitro; EMBO Journal 13: 258-268, 1994.

Vallet-Gely et al., Repression of phase-variable *cup* gene expression by H-NS-like proteins in *Pseudomonas aeruginosa*; PNAS 102: 11082-11087, 2005.

Van Brunt, Jennifer; Amplifying Genes: PCR and its Alternatives; Biotechnology 8: 291-294, 1990.

Westermark et al., Silencing and Activation of ClyA Cytotoxin Expression in *Escherichia coli*; Journal of Bacteriology 182: 6347-6357, 2000.

Williamson and Free; A truncated H-NS-like protein from enteropathogenic *Escherichia coli* acts as an H-NS antagonist, Molucler Microbiology 55: 808-827, 2005.

Wu and Wallace; Specificity of the nick-closing activity of bacteriophage T4 DNA ligase, Gene 4: 245-254, 1989.

Wyborn et al.; Regulation of *Escherichia coli* Hemolysin E Expression by H-NS and *Salmonella* SylA, Journal of Bacteriology 186: 1620-1628, 2004.

Yang et al.; Normalization for cDNA microarray data: a robust composite method addressing single and multiple slide systematic variation, Nucleic Acids Research 30: No. 4e15, 2002.

Yang et al.; The H-NS protein represses transcription of the *eltAB* operon, which encodes hear-labile enterotoxin in enterotoxigenic *Escherichia coli*, by binding to regions downstream of the promoter, Microbiology 151: 1199-1208, 2005.

Yu and DiRita; Regulation of gene expression in *Vibrio cholerae* by ToxT involves both antirepression and RNA polymerases stimulation, Molecular Microbiology, 43: 119-134, 2002.

Zilberman and Henikoff; Silencing of transposons in plant genomes: kick them when they're down, Genome Biology 5: 249, 2004.

Zimmerman; Cooperative transitions of isolated *Escherichia coli* nucleoids: Implications for the Nucleoid as a cellular phase, Journal of Structural Biology 153: 160-175, 2006.

Brosius. "Plasmid vectors for the selection of promoters." Gene 27:151-160 (1984).

Casadaban. "Fusion of the *Escherichia coli* lac Genes to the ara Promoter: A General Technique Using Bacteriophage Mu-1 Insertions." PNAS 72:809-813 (1975).

Casadaban et al. "Analysis of Gene control Signals by DNA Fusion and Cloning in *Escherichia coli*." J Mol Biol 138:179-207 (1980).

Goldfarb et al. "Expression of Tn9-derived chloramphenicol resistance in *Bacillus subtilis*." Nature 293:309-311 (1981).

Hirano et al. "Construction and characterization of plasmid and lambda phage vector systems for study of transcriptional control in *Escherichia coli*." Gene 57:89-99 (1987).

Lodge et al. "Comparison of promoter activities in *Escherichia coli* and *Psudomonas aeruginosa*: use of a new broad-host-range promoter-probe plasmid." FEMS Microbiology Letters 67:221-226 (1990).

* cited by examiner

| Gene | Protein – Accession Numbers | organism |
|---|---|---|
| rcd | PWQRRMP | Plasmid pWQ799 (ColE1 plasmid) |
| hns | NP_415753.1 | E. coli K12 genome |
| stpA | NP_417155.1 | E. coli K12 genome |
| hha | NP_414993.1 | E. coli K12 genome |
| ydgT | NP_416142.1 | E. coli K12 genome |
| abrB | NP_387918 | Bacillus subtilis str. 168 genome |
| abh | NP_389331 | Bacillus subtilis str. 168 genome |
| hbsU | NP_390160 | Bacillus subtilis str. 168 genome |
| mvaT | NP_253005 | Pseudomonas aeruginosa PAO1 genome |
| mvaU | NP_251357 | Pseudomonas aeruginosa PAO1 genome |
| bpH3 | NP_881493 | Bordetella pertussis Tohama I genome |
| xrvA | YP_451617 | Xanthomonas oryzae genome |
| xrvA | ZP_00682407 | Xylella fastidiosa Ann-1 genome |
| csgA | NP_415560.1 | E. coli K12 genome |
| csgB | NP_415559.1 | E. coli K12 genome |
| hdeA | NP_417967.1 | E. coli K12 genome |
| hdeB | NP_417966.2 | E. coli K12 genome |
| osmY | NP_418793.1 | E. coli K12 genome |
| phoP | NP_415648.1 | E. coli K12 genome |

Figure 2.

| Protein ID (accession) | Bacterial Species | Annotation |
|---|---|---|
| 120609838 | Acidovorax avenae subsp. citrulli AAC00-1 | histone family protein nucleoid-structuring protein H-NS |
| 120611248 | Acidovorax avenae subsp. citrulli AAC00-1 | histone family protein nucleoid-structuring protein H-NS |
| 110592813 | Acidovorax sp. JS42 | Histone-like nucleoid-structuring protein H-NS |
| 110595049 | Acidovorax sp. JS42 | Histone-like nucleoid-structuring protein H-NS |
| 30140442 | Acinetobacter sp. 20 | H-NSa protein |
| 50083565 | Acinetobacter sp. ADP1 | putative DNA binding protein |
| 32034774 | Actinobacillus pleuropneumoniae serovar 1 str. 4074 | COG2916: DNA-binding protein H-NS |
| 75431573 | Actinobacillus succinogenes 130Z | DNA-binding protein H-ns-like |
| 20196545 | Aeromonas hydrophila | histone-like nucleoid structuring protein |
| 117617525 | Aeromonas hydrophila subsp. hydrophila ATCC 7966 | DNA-binding protein StpA |
| 117618168 | Aeromonas hydrophila subsp. hydrophila ATCC 7966 | DNA-binding protein StpA |
| 117619452 | Aeromonas hydrophila subsp. hydrophila ATCC 7966 | DNA-binding protein Hns |
| 110832866 | Alcanivorax borkumensis SK2 | DNA-binding protein H-NS |
| 114321135 | Alkalilimnicola ehrlichei MLHE-1 | histone family protein nucleoid-structuring protein H-NS |
| 114772459 | alpha proteobacterium HTCC2255 | DNA-binding protein, H-NS family |
| 88796126 | Alteromonas macleodii 'Deep ecotype' | DNA-binding protein, H-NS family |
| 119896485 | Azoarcus sp. BH72 | putative trans-acting regulatory protein HvrA |
| 119899510 | Azoarcus sp. BH72 | putative trans-acting regulatory protein HvrA |
| 56475616 | Azoarcus sp. EbN1 | DNA-binding protein, similar to histone-like nucleoid-structuring protein H-NS |
| 56478800 | Azoarcus sp. EbN1 | putative HNS-like transcription regulator protein |
| 56478806 | Azoarcus sp. EbN1 | predicted DNA-binding protein H-NS |
| 56478831 | Azoarcus sp. EbN1 | putative HNS-like transcription regulator protein |
| 56478841 | Azoarcus sp. EbN1 | HNS-like transcription regulator protein |
| 58616281 | Azoarcus sp. EbN1 | histone-like nucleoid-structuring protein H-NS |
| 58616501 | Azoarcus sp. EbN1 | predicted histone-like nucleoid-structuring protein |
| 67156341 | Azotobacter vinelandii AvOP | transcriptional regulator, putative |
| 49476208 | Bartonella henselae str. Houston-1 | korB protein |
| 49474730 | Bartonella quintana str. Toulouse | Trans-acting regulatory protein hvrA |
| 32328571 | Bartonella tribocorum | KorB protein |
| 94676809 | Baumannia cicadellinicola str. Hc (Homalodisca coagulata) | DNA-binding protein H-NS |
| 115423233 | Bordetella avium 197N | DNA-binding protein (histone) |
| 33600917 | Bordetella bronchiseptica RB50 | putative DNA-binding protein (histone) |

Figure 3.

| | | |
|---|---|---|
| 33597073 | Bordetella parapertussis 12822 | putative DNA-binding protein (histone) |
| 33593849 | Bordetella pertussis Tohama I | putative DNA-binding protein (histone) |
| 118698000 | Burkholderia ambifaria MC40-6 | histone-like nucleoid-structuring protein H-NS |
| 118698073 | Burkholderia ambifaria MC40-6 | histone-like nucleoid-structuring protein H-NS |
| 118698237 | Burkholderia ambifaria MC40-6 | histone-like nucleoid-structuring protein H-NS |
| 118698482 | Burkholderia ambifaria MC40-6 | histone-like nucleoid-structuring protein H-NS |
| 118698636 | Burkholderia ambifaria MC40-6 | H-NS histone family protein |
| 118699073 | Burkholderia ambifaria MC40-6 | histone-like nucleoid-structuring protein H-NS |
| 118699081 | Burkholderia ambifaria MC40-6 | Histone-like nucleoid-structuring protein H-NS |
| 118699110 | Burkholderia ambifaria MC40-6 | histone-like nucleoid-structuring protein H-NS |
| 118700231 | Burkholderia ambifaria MC40-6 | histone-like nucleoid-structuring protein H-NS |
| 118700263 | Burkholderia ambifaria MC40-6 | histone-like nucleoid-structuring protein H-NS |
| 116687296 | Burkholderia cenocepacia HI2424 | histone family protein nucleoid-structuring protein H-NS |
| 118709263 | Burkholderia cenocepacia MCO-3 | Histone-like nucleoid-structuring protein H-NS |
| 118709419 | Burkholderia cenocepacia MCO-3 | histone-like nucleoid-structuring protein H-NS |
| 118711070 | Burkholderia cenocepacia MCO-3 | histone-like nucleoid-structuring protein H-NS |
| 118711437 | Burkholderia cenocepacia MCO-3 | histone-like nucleoid-structuring protein H-NS |
| 118711649 | Burkholderia cenocepacia MCO-3 | histone-like nucleoid-structuring protein H-NS |
| 118711679 | Burkholderia cenocepacia MCO-3 | histone-like nucleoid-structuring protein H-NS |
| 118712669 | Burkholderia cenocepacia MCO-3 | histone-like nucleoid-structuring protein H-NS |
| 118712732 | Burkholderia cenocepacia MCO-3 | histone-like nucleoid-structuring protein H-NS |
| 118713305 | Burkholderia cenocepacia MCO-3 | histone-like nucleoid-structuring protein H-NS |
| 118714246 | Burkholderia cenocepacia MCO-3 | histone-like nucleoid-structuring protein H-NS |
| 118714594 | Burkholderia cenocepacia MCO-3 | histone-like nucleoid-structuring protein H-NS |
| 84356304 | Burkholderia cenocepacia PC184 | COG2916: DNA-binding protein H-NS |
| 115359449 | Burkholderia cepacia AMMD | H-NS histone family protein |
| 115360932 | Burkholderia cepacia AMMD | histone family protein nucleoid-structuring protein H-NS |
| 115361123 | Burkholderia cepacia AMMD | histone family protein nucleoid-structuring protein H-NS |
| 84358562 | Burkholderia dolosa AUO158 | COG2916: DNA-binding protein H-NS |
| 84363476 | Burkholderia dolosa AUO158 | COG2916: DNA-binding protein H-NS |
| 84363515 | Burkholderia dolosa AUO158 | COG2916: DNA-binding protein H-NS |

Figure 3 continued

| | | |
|---|---|---|
| 100914811 | Burkholderia mallei 10399 | hypothetical protein Bmal10_03003906 |
| 100916824 | Burkholderia mallei 10399 | hypothetical protein Bmal10_03001890 |
| 53717351 | Burkholderia mallei ATCC 23344 | H-NS histone family protein |
| 53717437 | Burkholderia mallei ATCC 23344 | H-NS histone family protein |
| 83624781 | Burkholderia mallei JHU | COG2916: DNA-binding protein H-NS |
| 118715625 | Burkholderia multivorans ATCC 17616 | histone family protein nucleoid-structuring protein H-NS |
| 118716459 | Burkholderia multivorans ATCC 17616 | histone family protein nucleoid-structuring protein H-NS |
| 118718150 | Burkholderia multivorans ATCC 17616 | histone family protein nucleoid-structuring protein H-NS |
| 118720037 | Burkholderia multivorans ATCC 17616 | histone family protein nucleoid-structuring protein H-NS |
| 118720069 | Burkholderia multivorans ATCC 17616 | histone family protein nucleoid-structuring protein H-NS |
| 118720122 | Burkholderia multivorans ATCC 17616 | histone family protein nucleoid-structuring protein H-NS |
| 118720217 | Burkholderia multivorans ATCC 17616 | histone family protein nucleoid-structuring protein H-NS |
| 118721142 | Burkholderia multivorans ATCC 17616 | hypothetical protein BmulDRAFT_0007 |
| 118028285 | Burkholderia phymatum STM815 | histone-like nucleoid-structuring protein H-NS |
| 118029613 | Burkholderia phymatum STM815 | histone-like nucleoid-structuring protein H-NS |
| 118031161 | Burkholderia phymatum STM815 | histone-like nucleoid-structuring protein H-NS |
| 118031526 | Burkholderia phymatum STM815 | histone-like nucleoid-structuring protein H-NS |
| 118031905 | Burkholderia phymatum STM815 | histone-like nucleoid-structuring protein H-NS |
| 118032326 | Burkholderia phymatum STM815 | histone-like nucleoid-structuring protein H-NS |
| 118034461 | Burkholderia phymatum STM815 | histone-like nucleoid-structuring protein H-NS |
| 118035529 | Burkholderia phytofirmans PsJN | conserved hypothetical protein |
| 118036375 | Burkholderia phytofirmans PsJN | histone-like nucleoid-structuring protein H-NS |
| 118036619 | Burkholderia phytofirmans PsJN | histone-like nucleoid-structuring protein H-NS |
| 118037412 | Burkholderia phytofirmans PsJN | histone-like nucleoid-structuring protein H-NS |
| 118039453 | Burkholderia phytofirmans PsJN | histone-like nucleoid-structuring protein H-NS |
| 118039575 | Burkholderia phytofirmans PsJN | histone-like nucleoid-structuring protein H-NS |
| 118040197 | Burkholderia phytofirmans PsJN | histone-like nucleoid-structuring protein H-NS |
| 118040304 | Burkholderia phytofirmans PsJN | histone-like nucleoid-structuring protein H-NS |
| 118044391 | Burkholderia phytofirmans PsJN | histone-like nucleoid-structuring protein H-NS |
| 118044834 | Burkholderia phytofirmans PsJN | histone-like nucleoid-structuring protein H-NS |

Figure 3 continued

| | | |
|---|---|---|
| 37729606 | Burkholderia pseudomallei | BphA |
| 116238651 | Burkholderia pseudomallei 1106a | hypothetical protein Bpse11_03000629 |
| 116238669 | Burkholderia pseudomallei 1106a | hypothetical protein Bpse11_03000647 |
| 116240432 | Burkholderia pseudomallei 1106a | hypothetical protein Bpse11_03002434 |
| 116261335 | Burkholderia pseudomallei 1106a | hypothetical protein Bpse11_03003456 |
| 116261534 | Burkholderia pseudomallei 1106a | hypothetical protein Bpse11_03003658 |
| 116262220 | Burkholderia pseudomallei 1106a | hypothetical protein Bpse11_03004358 |
| 116262536 | Burkholderia pseudomallei 1106a | hypothetical protein Bpse11_03004681 |
| 116263095 | Burkholderia pseudomallei 1106a | hypothetical protein Bpse11_03005252 |
| 82537499 | Burkholderia pseudomallei 1106b | hypothetical protein Bpse110_02001089 |
| 99906533 | Burkholderia pseudomallei 1655 | hypothetical protein Bpse1_03005505 |
| 99912487 | Burkholderia pseudomallei 1655 | hypothetical protein Bpse1_03001421 |
| 76808711 | Burkholderia pseudomallei 1710b | BphA |
| 76810880 | Burkholderia pseudomallei 1710b | H-NS histone family protein |
| 76811574 | Burkholderia pseudomallei 1710b | H-NS histone family protein |
| 76817328 | Burkholderia pseudomallei 1710b | HNS-like transcription regulator protein |
| 76817372 | Burkholderia pseudomallei 1710b | H-NS histone family protein |
| 76817520 | Burkholderia pseudomallei 1710b | H-NS histone family protein |
| 76817530 | Burkholderia pseudomallei 1710b | H-NS histone family protein |
| 76817770 | Burkholderia pseudomallei 1710b | H-NS histone family protein |
| 67734366 | Burkholderia pseudomallei 668 | hypothetical protein Bpse6_01005507 |
| 67737278 | Burkholderia pseudomallei 668 | COG2916: DNA-binding protein H-NS |
| 53719283 | Burkholderia pseudomallei K96243 | putative DNA-biding protein, H-NS-like |
| 53719321 | Burkholderia pseudomallei K96243 | putative HNS-like protein |
| 53721100 | Burkholderia pseudomallei K96243 | H-NS-like DNA-binding protein |
| 53721821 | Burkholderia pseudomallei K96243 | H-NS-like protein |
| 53721873 | Burkholderia pseudomallei K96243 | hypothetical protein BPSS0846 |
| 78059715 | Burkholderia sp. 383 | Histone-like nucleoid-structuring protein H-NS |
| 78060496 | Burkholderia sp. 383 | Histone-like nucleoid-structuring protein H-NS |
| 78060562 | Burkholderia sp. 383 | Histone-like nucleoid-structuring protein H-NS |
| 78060692 | Burkholderia sp. 383 | Histone-like nucleoid-structuring protein H-NS |
| 78060985 | Burkholderia sp. 383 | Histone-like nucleoid-structuring protein H-NS |
| 78062076 | Burkholderia sp. 383 | Histone-like nucleoid-structuring protein H-NS |
| 78062683 | Burkholderia sp. 383 | Histone-like nucleoid-structuring protein H-NS |
| 78064828 | Burkholderia sp. 383 | Histone-like nucleoid-structuring protein H-NS |
| 78064861 | Burkholderia sp. 383 | Histone-like nucleoid-structuring protein H-NS |
| 83716046 | Burkholderia thailandensis E264 | H-NS histone family protein |
| 83716776 | Burkholderia thailandensis E264 | H-NS histone family protein |
| 83717611 | Burkholderia thailandensis E264 | DNA-binding protein BprA |
| 83717705 | Burkholderia thailandensis E264 | H-NS histone family protein |
| 83717865 | Burkholderia thailandensis E264 | H-NS histone family protein |
| 83718376 | Burkholderia thailandensis E264 | H-NS histone family protein |
| 83718508 | Burkholderia thailandensis E264 | DNA-binding protein BprA |
| 83719263 | Burkholderia thailandensis E264 | H-NS histone family protein |

Figure 3 continued

| | | |
|---|---|---|
| 83719804 | Burkholderia thailandensis E264 | H-NS histone family protein |
| 83719866 | Burkholderia thailandensis E264 | DNA-binding protein BprA |
| 83721381 | Burkholderia thailandensis E264 | H-NS histone family protein |
| 67542224 | Burkholderia vietnamiensis G4 | Histone-like nucleoid-structuring protein H-NS |
| 67542272 | Burkholderia vietnamiensis G4 | Histone-like nucleoid-structuring protein H-NS |
| 67542687 | Burkholderia vietnamiensis G4 | Histone-like nucleoid-structuring protein H-NS |
| 67542754 | Burkholderia vietnamiensis G4 | Histone-like nucleoid-structuring protein H-NS |
| 67543171 | Burkholderia vietnamiensis G4 | Histone-like nucleoid-structuring protein H-NS |
| 67543673 | Burkholderia vietnamiensis G4 | Histone-like nucleoid-structuring protein H-NS |
| 67544313 | Burkholderia vietnamiensis G4 | Histone-like nucleoid-structuring protein H-NS |
| 67544316 | Burkholderia vietnamiensis G4 | Histone-like nucleoid-structuring protein H-NS |
| 67547457 | Burkholderia vietnamiensis G4 | Histone-like nucleoid-structuring protein H-NS |
| 67547837 | Burkholderia vietnamiensis G4 | Histone-like nucleoid-structuring protein H-NS |
| 67547894 | Burkholderia vietnamiensis G4 | Histone-like nucleoid-structuring protein H-NS |
| 67547950 | Burkholderia vietnamiensis G4 | putative hns-like transcription regulator protein |
| 67548447 | Burkholderia vietnamiensis G4 | Histone-like nucleoid-structuring protein H-NS |
| 67548480 | Burkholderia vietnamiensis G4 | Histone-like nucleoid-structuring protein H-NS |
| 67549076 | Burkholderia vietnamiensis G4 | Histone-like nucleoid-structuring protein H-NS |
| 67549820 | Burkholderia vietnamiensis G4 | Histone-like nucleoid-structuring protein H-NS |
| 67549917 | Burkholderia vietnamiensis G4 | Histone-like nucleoid-structuring protein H-NS |
| 91777162 | Burkholderia xenovorans LB400 | putative H-NS-like transcription regulator |
| 91779312 | Burkholderia xenovorans LB400 | putative histone-like protein |
| 91779936 | Burkholderia xenovorans LB400 | Histone-like nucleoid-structuring protein H-NS |
| 91781525 | Burkholderia xenovorans LB400 | Putative HNS-like transcriptional regulator |
| 91785665 | Burkholderia xenovorans LB400 | HNS-like transcriptional regulator |
| 71892210 | Candidatus Blochmannia pennsylvanicus str. BPEN | DNA-binding protein HLP-II (HU, BH2, HD, NS) |
| 58003974 | Cellulomonas flavigena | putative transcriptional regulator |
| 67917974 | Chlorobium limicola DSM 245 | hypothetical protein ClimDRAFT_0501 |
| 67919648 | Chlorobium limicola DSM 245 | Histone-like nucleoid-structuring protein H-NS |
| 34496698 | Chromobacterium violaceum ATCC 12472 | probable trans-acting regulatory HvrA protein |
| 34496818 | Chromobacterium violaceum ATCC 12472 | probable trans-acting regulatory HvrA protein |
| 92113776 | Chromohalobacter salexigens DSM | transcriptional regulator MvaT, P16 |

Figure 3 continued

| | | |
|---:|---|---|
| | 3043 | subunit |
| 15723902 | Citrobacter rodentium | LEE-encoded regulator |
| 118048975 | Comamonas testosteroni KF-1 | histone-like nucleoid-structuring protein H-NS |
| 118052960 | Comamonas testosteroni KF-1 | histone-like nucleoid-structuring protein H-NS |
| 118052984 | Comamonas testosteroni KF-1 | histone-like nucleoid-structuring protein H-NS |
| 118053638 | Comamonas testosteroni KF-1 | histone-like nucleoid-structuring protein H-NS |
| 118054051 | Comamonas testosteroni KF-1 | histone-like nucleoid-structuring protein H-NS |
| 71908141 | Dechloromonas aromatica RCB | Histone-like nucleoid-structuring protein H-NS |
| 118729492 | Delftia acidovorans SPH-1 | histone-like nucleoid-structuring protein H-NS |
| 118729699 | Delftia acidovorans SPH-1 | histone-like nucleoid-structuring protein H-NS |
| 118730283 | Delftia acidovorans SPH-1 | histone-like nucleoid-structuring protein H-NS |
| 118732363 | Delftia acidovorans SPH-1 | histone-like nucleoid-structuring protein H-NS |
| 118732536 | Delftia acidovorans SPH-1 | histone-like nucleoid-structuring protein H-NS |
| 118733223 | Delftia acidovorans SPH-1 | histone-like nucleoid-structuring protein H-NS |
| 118733879 | Delftia acidovorans SPH-1 | histone-like nucleoid-structuring protein H-NS |
| 118733921 | Delftia acidovorans SPH-1 | histone-like nucleoid-structuring protein H-NS |
| 118734544 | Delftia acidovorans SPH-1 | histone-like nucleoid-structuring protein H-NS |
| 118734589 | Delftia acidovorans SPH-1 | histone-like nucleoid-structuring protein H-NS |
| 51244408 | Desulfotalea psychrophila LSv54 | similar to DNA-binding protein H-NS |
| 118736218 | Dinoroseobacter shibae DFL 12 | histone family protein nucleoid-structuring protein H-NS |
| 30141199 | Enterobacter sp. 22 | H-NSb protein |
| 118742462 | Enterobacter sp. 638 | histone-like nucleoid-structuring protein H-NS |
| 118743237 | Enterobacter sp. 638 | histone-like nucleoid-structuring protein H-NS |
| 44680180 | Erwinia amylovora | histone-like nucleoid structuring protein |
| 70909461 | Erwinia amylovora | heat-stable nucleoid-structuring protein |
| 80750630 | Erwinia amylovora | heat-stable nucleoid-structuring protein |
| 50120597 | Erwinia carotovora subsp. atroseptica SCRI1043 | DNA-binding protein Hns |
| 50121256 | Erwinia carotovora subsp. atroseptica SCRI1043 | DNA-binding protein Hns |
| 50121817 | Erwinia carotovora subsp. atroseptica SCRI1043 | DNA-binding protein Hns |
| 2956659 | Erwinia chrysanthemi | HNS regulatory protein |
| 14970554 | Erwinia chrysanthemi | H-NS protein |
| 27228692 | Erwinia pyrifoliae | histone nucleoid structuring protein |

Figure 3 continued

| | | |
|---|---|---|
| 31790977 | Erwinia sp. Ejp 556 | Hns |
| 41738 | Escherichia coli | DNA-binding protein HN-S |
| 43078 | Escherichia coli | H-ns |
| 2865271 | Escherichia coli | Orf1 |
| 17736922 | Escherichia coli | LEE encoded regulator |
| 18034563 | Escherichia coli | Ler |
| 54311595 | Escherichia coli | Ler protein |
| 57434476 | Escherichia coli | LEE encoded regulator |
| 86212198 | Escherichia coli | TPA: putative transcriptional repressor |
| 92110308 | Escherichia coli | DNA-binding protein H-NS |
| 110084060 | Escherichia coli | hypothetical protein |
| 113706769 | Escherichia coli | KorB |
| 83585164 | Escherichia coli 101-1 | COG2916: DNA-binding protein H-NS |
| 110642099 | Escherichia coli 536 | putative DNA-binding protein |
| 110642792 | Escherichia coli 536 | DNA-binding protein StpA |
| 75513238 | Escherichia coli 53638 | COG2916: DNA-binding protein H-NS |
| 117623452 | Escherichia coli APEC O1 | H-ns |
| 117624904 | Escherichia coli APEC O1 | DNA-binding protein StpA |
| 75214588 | Escherichia coli E110019 | COG2916: DNA-binding protein H-NS |
| 75234114 | Escherichia coli E110019 | COG2916: DNA-binding protein H-NS |
| 75259889 | Escherichia coli E22 | COG2916: DNA-binding protein H-NS |
| 68249828 | Haemophilus influenzae 86-028NP | DNA-binding protein H-NS homolog |
| 113460930 | Haemophilus somnus 129PT | DNA-binding protein H-NS |
| 46156060 | Haemophilus somnus 2336 | COG2916: DNA-binding protein H-NS |
| 83644368 | Hahella chejuensis KCTC 2396 | hypothetical protein HCH_01520 |
| 83645185 | Hahella chejuensis KCTC 2396 | hypothetical protein HCH_02377 |
| 83646071 | Hahella chejuensis KCTC 2396 | DNA-binding protein H-NS |
| 83647200 | Hahella chejuensis KCTC 2396 | hypothetical protein HCH_04508 |
| 88948280 | Halorhodospira halophila SL1 | Histone-like nucleoid-structuring protein H-NS |
| 88949499 | Halorhodospira halophila SL1 | Histone-like nucleoid-structuring protein H-NS |
| 85711992 | Idiomarina baltica OS145 | Histone-like protein |
| 56459990 | Idiomarina loihiensis L2TR | Histone-like protein |
| 25294382 | imported | DNA-binding protein H-ns |
| 89053289 | Jannaschia sp. CCS1 | histone-like nucleoid-structuring protein H-NS |
| 89057715 | Jannaschia sp. CCS1 | histone-like nucleoid-structuring protein H-NS |
| 28201198 | Janthinobacterium sp. J3 | DNA-binding protein |
| 38639648 | Klebsiella pneumoniae | H-ns |
| 84515891 | Loktanella vestfoldensis SKA53 | DNA-binding protein, H-NS family |
| 84516490 | Loktanella vestfoldensis SKA53 | Histone-like protein of HNS family |
| 52425377 | Mannheimia succiniciproducens MBEL55E | Hns protein |
| 120536871 | Marinobacter aquaeolei VT8 | hypothetical protein Maqu_4162 |
| 120555519 | Marinobacter aquaeolei VT8 | transcriptional regulator MvaT, P16 subunit |
| 87120343 | Marinomonas sp. MED121 | DNA-binding protein H-NS |
| 118747855 | Marinomonas sp. MWYL1 | histone-like nucleoid-structuring protein H-NS |
| 53803840 | Methylococcus capsulatus str. Bath | regulator protein, putative |
| 92118541 | Nitrobacter hamburgensis X14 | histone-like nucleoid-structuring protein |

Figure 3 continued

| | | |
|---|---|---|
| 92118542 | Nitrobacter hamburgensis X14 | H-NS histone-like nucleoid-structuring protein H-NS |
| 85717220 | Nitrobacter sp. Nb-311A | regulator protein, putative |
| 88812990 | Nitrococcus mobilis Nb-231 | probable trans-acting regulatory HvrA protein |
| 88813017 | Nitrococcus mobilis Nb-231 | Histone-like nucleoid-structuring protein H-NS |
| 30249318 | Nitrosomonas europaea ATCC 19718 | H-NS histone family |
| 114331951 | Nitrosomonas eutropha C91 | histone family protein nucleoid-structuring protein H-NS |
| 84499595 | Oceanicola batsensis HTCC2597 | Histone-like protein of HNS family protein |
| 84503345 | Oceanicola batsensis HTCC2597 | HNS family histone-like protein |
| 89068115 | Oceanicola granulosus HTCC2516 | DNA-binding protein, H-NS family protein |
| 89094111 | Oceanospirillum sp. MED92 | DNA-binding protein Hns |
| 69935546 | Paracoccus denitrificans PD1222 | Histone-like nucleoid-structuring protein H-NS |
| 119384285 | Paracoccus denitrificans PD1222 | histone family protein nucleoid-structuring protein H-NS |
| 119385506 | Paracoccus denitrificans PD1222 | histone family protein nucleoid-structuring protein H-NS |
| 119385878 | Paracoccus denitrificans PD1222 | histone family protein nucleoid-structuring protein H-NS |
| 119386063 | Paracoccus denitrificans PD1222 | histone family protein nucleoid-structuring protein H-NS |
| 15602737 | Pasteurella multocida subsp. multocida str. Pm70 | Hns |
| 68550838 | Pelodictyon phaeoclathratiforme BU-1 | putative hns-like transcription regulator protein |
| 118614763 | Photobacterium damselae subsp. piscicida | DNA binding protein, H-NS-like protein |
| 90411629 | Photobacterium profundum 3TCK | putative DNA-binding protein H-NS |
| 54308275 | Photobacterium profundum SS9 | putative DNA-binding protein H-NS |
| 89072388 | Photobacterium sp. SKA34 | putative DNA-binding protein H-NS |
| 89075748 | Photobacterium sp. SKA34 | putative DNA-binding protein H-NS |
| 37525231 | Photorhabdus luminescens subsp. laumondii TTO1 | hypothetical protein plu1264 |
| 84710140 | Polaromonas naphthalenivorans CJ2 | Histone-like nucleoid-structuring protein H-NS |
| 84710231 | Polaromonas naphthalenivorans CJ2 | Histone-like nucleoid-structuring protein H-NS |
| 84713641 | Polaromonas naphthalenivorans CJ2 | Histone-like nucleoid-structuring protein H-NS |
| 84713859 | Polaromonas naphthalenivorans CJ2 | Histone-like nucleoid-structuring protein H-NS |
| 84716033 | Polaromonas naphthalenivorans CJ2 | Histone-like nucleoid-structuring protein H-NS |
| 91789824 | Polaromonas sp. JS666 | histone-like nucleoid-structuring protein H-NS |
| 116270384 | Polynucleobacter sp. QLW-P1DMWA-1 | histone-like nucleoid-structuring protein H-NS |
| 7341304 | Proteus mirabilis | histone-like nucleoid structuring protein |
| 109898465 | Pseudoalteromonas atlantica T6c | histone-like nucleoid-structuring protein |

Figure 3 continued

| | | |
|---|---|---|
| 84316844 | Pseudomonas aeruginosa C3719 | H-NS |
| 94412900 | Pseudomonas aeruginosa PA7 | hypothetical protein PaerC_01005374 |
| 94413980 | Pseudomonas aeruginosa PA7 | hypothetical protein PaerP_01005314 |
| | | hypothetical protein PaerP_01004250 |
| 116050654 | Pseudomonas aeruginosa UCBPP-PA14 | putative transcriptional regulator |
| 116052349 | Pseudomonas aeruginosa UCBPP-PA14 | transcriptional regulator MvaT, P16 subunit |
| 104780362 | Pseudomonas entomophila L48 | transcriptional regulator MvaT, P16 subunit |
| 104782263 | Pseudomonas entomophila L48 | transcriptional regulator MvaT, P16 subunit |
| 60326835 | Pseudomonas fluorescens | MvaV |
| 70730755 | Pseudomonas fluorescens Pf-5 | transcriptional regulator, putative |
| 70732112 | Pseudomonas fluorescens Pf-5 | transcriptional regulator, putative |
| 70732304 | Pseudomonas fluorescens Pf-5 | transcriptional regulator, putative |
| 77459020 | Pseudomonas fluorescens PfO-1 | hypothetical protein Pfl_2795 |
| 77459146 | Pseudomonas fluorescens PfO-1 | transcriptional regulator, putative |
| 77459236 | Pseudomonas fluorescens PfO-1 | hypothetical protein Pfl_3014 |
| 77460658 | Pseudomonas fluorescens PfO-1 | transcriptional regulator, putative |
| 118057269 | Pseudomonas mendocina ymp | transcriptional regulator, putative |
| 1184831 | Pseudomonas mevalonii | heteromeric transcriptional activator MvaT P16 subunit |
| 111116399 | Pseudomonas putida | putative transcriptional regulator protein |
| 82735262 | Pseudomonas putida F1 | conserved hypothetical protein |
| 82735427 | Pseudomonas putida F1 | transcriptional regulator MvaT, P16 subunit, putative |
| 82736524 | Pseudomonas putida F1 | transcriptional regulator MvaT, P16 subunit, putative |
| 82738273 | Pseudomonas putida F1 | conserved hypothetical protein |
| 82740011 | Pseudomonas putida F1 | transcriptional regulator MvaT, P16 subunit |
| 26988100 | Pseudomonas putida KT2440 | transcriptional regulator MvaT, P16 subunit |
| 26989666 | Pseudomonas putida KT2440 | transcriptional regulator MvaT, P16 subunit, putative |
| 26990401 | Pseudomonas putida KT2440 | transcriptional regulator MvaT, P16 subunit, putative |
| 26990470 | Pseudomonas putida KT2440 | transcriptional regulator MvaT, P16 subunit, putative |
| 119856845 | Pseudomonas putida W619 | transcriptional regulator MvaT, P16 subunit |
| 119857251 | Pseudomonas putida W619 | conserved hypothetical protein |
| 119857595 | Pseudomonas putida W619 | transcriptional regulator MvaT, P16 subunit, putative |
| 119857720 | Pseudomonas putida W619 | transcriptional regulator MvaT, P16 subunit, putative |
| 119857916 | Pseudomonas putida W619 | transcriptional regulator, putative |
| 27228562 | Pseudomonas resinovorans | transcriptional regulator |
| 38201477 | Pseudomonas sp. Y1000 | H-NS |
| 68637877 | Pseudomonas syringae pv. phaseolicola | MvaT-like transcriptional regulator |
| 71734419 | Pseudomonas syringae pv. phaseolicola 1448A | transcriptional regulator, putative |

Figure 3 continued

| | | |
|---|---|---|
| 71734755 | Pseudomonas syringae pv. phaseolicola 1448A | transcriptional regulator, putative |
| 71736002 | Pseudomonas syringae pv. phaseolicola 1448A | H-NS |
| 66043398 | Pseudomonas syringae pv. syringae B728a | hypothetical protein Psyr_0128 |
| 66046202 | Pseudomonas syringae pv. syringae B728a | transcriptional regulator, putative |
| 28867513 | Pseudomonas syringae pv. tomato str. DC3000 | hypothetical protein PSPTO_0281 |
| 28870276 | Pseudomonas syringae pv. tomato str. DC3000 | transcriptional regulator, putative |
| 28871296 | Pseudomonas syringae pv. tomato str. DC3000 | hypothetical protein PSPTO_4154 |
| 28871871 | Pseudomonas syringae pv. tomato str. DC3000 | hypothetical protein PSPTO_4755 |
| 93006781 | Psychrobacter cryohalolentis K5 | histone-like nucleoid-structuring protein H-NS |
| 25005278 | Psychrobacter sp. TAD1 | H-NSA |
| 38637844 | Ralstonia eutropha H16 | H-NS-like protein |
| 116694182 | Ralstonia eutropha H16 | H-NS-like DNA-binding protein |
| 116696192 | Ralstonia eutropha H16 | H-NS-like DNA-binding protein |
| 72383840 | Ralstonia eutropha JMP134 | Histone-like nucleoid-structuring protein H-NS |
| 72384153 | Ralstonia eutropha JMP134 | Histone-like nucleoid-structuring protein H-NS |
| 72384187 | Ralstonia eutropha JMP134 | Histone-like nucleoid-structuring protein H-NS |
| 73538815 | Ralstonia eutropha JMP134 | Histone-like nucleoid-structuring protein H-NS |
| 73539418 | Ralstonia eutropha JMP134 | Histone-like nucleoid-structuring protein H-NS |
| 94312609 | Ralstonia metallidurans CH34 | histone-like nucleoid-structuring protein H-NS |
| 94313857 | Ralstonia metallidurans CH34 | histone-like nucleoid-structuring protein H-NS |
| 94314481 | Ralstonia metallidurans CH34 | histone-like nucleoid-structuring protein H-NS |
| 17545586 | Ralstonia solanacearum GMI1000 | PUTATIVE HNS-LIKE TRANSCRIPTION REGULATOR PROTEIN |
| 17548250 | Ralstonia solanacearum GMI1000 | PUTATIVE HNS-LIKE TRANSCRIPTION REGULATOR PROTEIN |
| 17548556 | Ralstonia solanacearum GMI1000 | PUTATIVE HNS-LIKE TRANSCRIPTION REGULATOR PROTEIN |
| 17549319 | Ralstonia solanacearum GMI1000 | PUTATIVE HNS-LIKE TRANSCRIPTION REGULATOR PROTEIN |
| 83745692 | Ralstonia solanacearum UW551 | H-NS-like proteins |
| 83747664 | Ralstonia solanacearum UW551 | H-NS-like proteins |
| 83749515 | Ralstonia solanacearum UW551 | H-NS-like proteins |
| 77404698 | Rhodobacter sphaeroides 2.4.1 | DNA-binding protein, H-NS family |
| 77404699 | Rhodobacter sphaeroides 2.4.1 | Histone-like nucleoid-structuring protein H-NS |
| 77463568 | Rhodobacter sphaeroides 2.4.1 | Histone-like nucleoid-structuring protein H-NS |

Figure 3 continued

| | | |
|---|---|---|
| 83367349 | Rhodobacter sphaeroides ATCC 17025 | Histone-like nucleoid-structuring protein H-NS |
| 83367503 | Rhodobacter sphaeroides ATCC 17025 | Histone-like nucleoid-structuring protein H-NS |
| 83369474 | Rhodobacter sphaeroides ATCC 17025 | Histone-like nucleoid-structuring protein H-NS |
| 83370913 | Rhodobacter sphaeroides ATCC 17025 | Histone-like nucleoid-structuring protein H-NS |
| 83372082 | Rhodobacter sphaeroides ATCC 17029 | Histone-like nucleoid-structuring protein H-NS |
| 84685002 | Rhodobacterales bacterium HTCC2654 | Histone-like nucleoid-structuring protein H-NS |
| 89902290 | Rhodoferax ferrireducens T118 | histone-like nucleoid-structuring protein H-NS |
| 91977209 | Rhodopseudomonas palustris BisB5 | Histone-like nucleoid-structuring protein H-NS |
| 86138968 | Roseobacter sp. MED193 | DNA-binding protein, H-NS family protein |
| 83950163 | Roseovarius nubinhibens ISM | DNA-binding protein, H-NS family protein |
| 85707300 | Roseovarius sp. 217 | Histone-like nucleoid-structuring protein H-NS |
| 114764855 | Roseovarius sp. HTCC2601 | DNA-binding protein, H-NS family |
| 47573011 | Rubrivivax gelatinosus PM1 | COG2916: DNA-binding protein H-NS |
| 47574950 | Rubrivivax gelatinosus PM1 | COG2916: DNA-binding protein H-NS |
| 62180316 | Salmonella enterica subsp. enterica serovar Choleraesuis str. SC-B67 | DNA-binding protein HLP-II (HU, BH2, HD, NS); pleiotropic regulator |
| 62181302 | Salmonella enterica subsp. enterica serovar Choleraesuis str. SC-B67 | DNA-binding protein with chaperone activity |
| 18466572 | Salmonella enterica subsp. enterica serovar Typhi str. CT18 | putative DNA-binding protein |
| 10957353 | Salmonella typhi | 'DNA binding protein, H-NS-like' |
| 38347949 | Serratia marcescens | hn-s family DNA-binding protein |
| 118070209 | Serratia proteamaculans 568 | histone-like nucleoid-structuring protein H-NS |
| 119774305 | Shewanella amazonensis SB2B | DNA-binding protein, H-NS family |
| 113950087 | Shewanella baltica OS195 | histone-like nucleoid-structuring protein H-NS |
| 91793891 | Shewanella denitrificans OS217 | histone-like nucleoid-structuring protein H-NS |
| 114563914 | Shewanella frigidimarina NCIMB 400 | histone family protein nucleoid-structuring protein H-NS |
| 24374659 | Shewanella oneidensis MR-1 | DNA-binding protein, H-NS family |
| 118755340 | Shewanella pealeana ATCC 700345 | histone family protein nucleoid-structuring protein H-NS |
| 77816812 | Shewanella putrefaciens CN-32 | Histone-like nucleoid-structuring protein H-NS |
| 117919852 | Shewanella sp. ANA-3 | histone family protein nucleoid-structuring protein H-NS |
| 113969693 | Shewanella sp. MR-4 | histone family protein nucleoid-structuring protein H-NS |
| 114046922 | Shewanella sp. MR-7 | histone family protein nucleoid-structuring protein H-NS |
| 78367567 | Shewanella sp. PV-4 | Histone-like nucleoid-structuring protein H-NS |
| 120558407 | Shewanella sp. W3-18-1 | histone family protein nucleoid- |

Figure 3 continued

| | | |
|---|---|---|
| 118073872 | Shewanella woodyi ATCC 51908 | structuring protein H-NS histone-like nucleoid-structuring protein H-NS |
| 75175592 | Shigella boydii BS512 | COG2916: DNA-binding protein H-NS |
| 83569970 | Shigella dysenteriae 1012 | COG2916: DNA-binding protein H-NS |
| 47036 | Shigella flexneri | unnamed protein product |
| 24061775 | Shigella flexneri 2a | H-NS-like protein Sfh |
| 110806698 | Shigella flexneri 5 str. 8401 | DNA-binding protein stpA |
| 56695282 | Silicibacter pomeroyi DSS-3 | DNA-binding protein, H-NS family |
| 56696124 | Silicibacter pomeroyi DSS-3 | DNA-binding protein, H-NS family |
| 99078085 | Silicibacter sp. TM1040 | histone-like nucleoid-structuring protein H-NS |
| 85059348 | Sodalis glossinidius str. 'morsitans' | histone-like protein |
| 85060413 | Sodalis glossinidius str. 'morsitans' | DNA-binding protein |
| 119876660 | Stenotrophomonas maltophilia R551-3 | histone-like nucleoid-structuring protein H-NS |
| 119876830 | Stenotrophomonas maltophilia R551-3 | histone-like nucleoid-structuring protein H-NS |
| 83943858 | Sulfitobacter sp. EE-36 | DNA-binding protein, H-NS family protein |
| 83953499 | Sulfitobacter sp. NAS-14.1 | DNA-binding protein, H-NS family protein |
| 83956252 | Sulfitobacter sp. NAS-14.1 | Histone-like protein, HNS family protein |
| 49074262 | synthetic construct | PA2667 |
| 111611701 | Verminephrobacter eiseniae EF01-2 | bprA; HNS-like transcription regulator protein |
| 91226033 | Vibrio alginolyticus 12G01 | DNA-binding protein H-NS |
| 90577262 | Vibrio angustum S14 | putative DNA-binding protein H-NS |
| 90580083 | Vibrio angustum S14 | putative DNA-binding protein H-NS |
| 15641143 | Vibrio cholerae O1 biovar eltor str. N16961 | DNA-binding protein H-NS |
| 116216699 | Vibrio cholerae RC385 | hypothetical protein VchoR_02001553 |
| 116220444 | Vibrio cholerae V51 | hypothetical protein VchoV5_02001493 |
| 15723717 | Vibrio parahaemolyticus | DNA-binding protein H-NS |
| 73759934 | Vibrio parahaemolyticus | H-NS-like protein |
| 28897907 | Vibrio parahaemolyticus RIMD 2210633 | DNA-binding protein H-NS |
| 116183735 | Vibrio sp. Ex25 | hypothetical protein VEx2w_02003732 |
| 86147098 | Vibrio sp. MED222 | DNA-binding protein H-NS |
| 84391739 | Vibrio splendidus 12B01 | DNA-binding protein H-NS |
| 27366200 | Vibrio vulnificus CMCP6 | DNA-binding protein H-NS |
| 37679530 | Vibrio vulnificus YJ016 | DNA-binding protein H-NS |
| 32491116 | Wigglesworthia glossinidia endosymbiont of Glossina brevipalpis | hypothetical protein WGLp367 |
| 21242247 | Xanthomonas axonopodis pv. citri str. 306 | virulence regulator |
| 21244293 | Xanthomonas axonopodis pv. citri str. 306 | DNA-binding protein |
| 66768127 | Xanthomonas campestris pv. campestris str. 8004 | virulence regulator |
| 66769897 | Xanthomonas campestris pv. campestris str. 8004 | DNA-binding protein |
| 78048170 | Xanthomonas campestris pv. vesicatoria str. 85-10 | histone-like nucleoid-structuring protein |

Figure 3 continued

| | | |
|---|---|---|
| 78048964 | Xanthomonas campestris pv. vesicatoria str. 85-10 | putative histone-like nucleoid-structuring protein |
| 78049249 | Xanthomonas campestris pv. vesicatoria str. 85-10 | putative DNA-binding protein |
| 58580431 | Xanthomonas oryzae pv. oryzae KACC10331 | DNA-binding protein |
| 84622393 | Xanthomonas oryzae pv. oryzae MAFF 311018 | DNA-binding protein |
| 84624245 | Xanthomonas oryzae pv. oryzae MAFF 311018 | virulence regulator xrvA |
| 39939250 | Xenorhabdus nematophila | putative DNA-binding protein |
| 15837048 | Xylella fastidiosa 9a5c | DNA-binding protein |
| 15838094 | Xylella fastidiosa 9a5c | virulence regulator |
| 71898156 | Xylella fastidiosa Ann-1 | Histone-like nucleoid-structuring protein H-NS |
| 71899286 | Xylella fastidiosa Ann-1 | Histone-like nucleoid-structuring protein H-NS |
| 71899577 | Xylella fastidiosa Ann-1 | Histone-like nucleoid-structuring protein H-NS |
| 71900270 | Xylella fastidiosa Ann-1 | Histone-like nucleoid-structuring protein H-NS |
| 28198614 | Xylella fastidiosa Temecula1 | virulence regulator |
| 13561120 | Yersinia enterocolitica | H-NS protein |
| 37518426 | Yersinia enterocolitica | DNA binding protein |
| 77972682 | Yersinia frederiksenii ATCC 33641 | COG2916: DNA-binding protein H-NS |
| 77977792 | Yersinia intermedia ATCC 29909 | COG2916: DNA-binding protein H-NS |
| 77960741 | Yersinia mollaretii ATCC 43969 | COG2916: DNA-binding protein H-NS |
| 115347885 | Yersinia pestis CO92 | DNA-binding protein Hns |
| 117671832 | Yersinia pseudotuberculosis IP 31758 | hypothetical protein YpseI_02003920 |
| 117673591 | Yersinia pseudotuberculosis IP 31758 | hypothetical protein YpseI_02001796 |
| 51593962 | Yersinia pseudotuberculosis IP 32953 | DNA-binding protein |
| 123442 | | DNA-binding protein H-NS (Histone-like protein HLP-II) |
| 123444 | | DNA-binding protein H-NS (Histone-like protein HLP-II) |
| 1065292 | | Chain , H-Ns (Dna-Binding Domain) |
| 1170430 | | Trans-acting regulatory protein hvrA |
| 28373550 | | Chain B, Solution Structure Of The Oligomerization Domain Of The Bacterial Chromatin-Structuring Protein H-Ns |
| 28948872 | | Chain B, H-Ns Dimerization Motif |
| 39654396 | | Chain B, Crystal Structure Of The N-Terminal Dimerisation Domain Of Vich, The H-Ns Protein From Vibrio Cholerae |
| 62900113 | | DNA-binding protein H-NS (Histone-like protein HLP-II) (Protein H1) (Protein B1) |

Figure 3 continued

METHODS AND HOST CELLS FOR RECOMBINANT PROTEIN EXPRESSION

CROSS CLAIMS

This application claims benefit under 35 U.S.C. §119(e) to U.S. Provisional Application No. 60/885,198, filed Jan. 16, 2007, hereby incorporated by reference in its entirety.

STATEMENT OF GOVERNMENT RIGHTS

This invention was made with U.S. Government support under grants 5R01AI039557-10 and 5R01AI048622-05 awarded by the National Institutes of Health. The U.S. Government has certain rights in the invention.

FIELD

The present invention is directed to methods for expressing recombinant polypeptides in host cells and host cells for polypeptide expression.

BACKGROUND

More than 325 million people worldwide have been helped by the more than 155 recombinantly produced polypeptides and peptides (drugs and vaccines) currently approved by the United States Food and Drug Administration. In addition, there are more than 370 biotechnology drug products and vaccines currently in clinical trials targeting more than 200 diseases, including: various cancers, Alzheimer's disease, heart disease, diabetes, multiple sclerosis, AIDS and arthritis. However, development and manufacturing of therapeutically useful polypeptides has been hampered, in large part, by the limitations of the organisms currently used to express these exogenous polypeptides.

Unlike traditional small molecule therapeutic agents, which are produced through classical chemical synthesis, polypeptides are produced and purified from living cells in an inefficient and costly process. To generate large quantities of polypeptides for biotechnology applications, it is typically necessary to express a polypeptide as a "recombinant" product in an organism distinct from the original source (e.g., human polypeptide produced in a bacterial cell). This is necessary because it is often difficult to obtain adequate quantities of polypeptide from native sources. A number of systems have been developed for the expression of polypeptides in bacterial, yeast, insect and animal cells. When practical, bacterial expression systems are ideal because bacteria grow rapidly, bacterial growth medium is inexpensive and less prone to contamination, bacterial physiology is relatively well understood, and several strains of genetically modified bacteria have been developed to produce high-quality, intact recombinant polypeptides.

To express a recombinant polypeptide in a non-native organism, it is generally necessary to optimize the gene sequence. This optimization includes putting the gene under the control of a strong inducible promoter, adding sequences that facilitate purification and increase polypeptide stability, and altering rare codons within the coding sequence. Despite the development of techniques for polypeptide production in bacterial systems, it is still difficult to obtain high-yields of certain polypeptides. This is particularly true when attempting the production of polypeptides from higher organisms such as humans, due to small but significant differences in the structures of human and bacterial genes. A need exists for improved methods for expressing recombinant polypeptide in non-native organisms. The present invention addresses this and other needs.

SUMMARY

The present invention provides, inter alia, methods of expressing a polypeptide in a host cell. The methods comprise the steps of inhibiting the expression of at least one xenogeneic silencing protein that is endogenous to the host cell, and culturing the host cell under conditions that allow expression of the polypeptide. The methods can further comprise a step of introducing a recombinant expression cassette comprising a nucleic acid sequence that encodes a polypeptide for expression into the host cell.

The present invention also provides, inter alia, host cells for expressing foreign polypeptides. The host cells comprise a recombinant expression cassette comprising a nucleic acid sequence that encodes a polypeptide for expression. The host cell will have decreased expression of a xenogeneic silencing protein that is endogenous to the host cell.

In certain embodiments, the host cells of the present invention will be non-quiescent cells. For example, in certain aspects, the host cell will have normal expression levels of a rcd RNA, i.e., the rcd RNA will be absent or substantially absent from the host cell. The rcd locus is carried by ColE1 plasmids, which are not present in most bacterial cells. The sequence of plasmid ColE1 can be found at GenBank Accession Number NC 001371. According to Sharpe et al. (Microbiology 145:2135-44, 1999), the rcd RNA is contained within nt 3827-3968 of this sequence.

The host cells of the present invention include any host cells that can be used as expression systems to produce recombinant proteins. Exemplary host cells are bacterial host cells, such as, for example, E coli.

Expression of a xenogeneic silencing protein can be inhibited using any method known in the art. In certain aspects, a mutation in the gene that encodes the xenogeneic silencing protein will be introduced into the cell and the mutation will act to prevent production of the wild type xenogeneic silencing protein. For example, in certain embodiments, the mutation will cause the production of a truncated xenogeneic silencing protein that does not posses the same expression or activity level as the wild type protein. In certain other embodiments, the mutation will inhibit the production of xenogeneic silencing protein all together.

In certain embodiments, only one xenogeneic silencing protein will be inhibited. In other embodiments, the expression and/or activity of two or even more than two xenogeneic silencing protein will be inhibited. In certain aspects, the xenogeneic silencing protein will be a DNA binding protein or a protein that interacts with a DNA binding protein. The xenogeneic silencing protein can be, for example, H-NS protein, H-NS homologs, including H-NS paralogs or orthologs, H-NS like proteins, HN-S interactor proteins, H-NS homolog interactor proteins, and H-NS like interactor proteins. Exemplary xenogeneic silencing proteins include, for example, the StpA protein, Hha protein, YdgT protein, MvaT protein, and/or MvaU protein.

Additional mutations can be introduced into the host cells. These mutations can be, for example, for inhibiting the expression of an alternative sigma factor $\sigma^S$ polypeptide and/or alternative sigma factor $\sigma^S$ dependent polypeptide and/or virulence regulator polypeptide, PhoP. In certain embodiments, the expression of these polypeptides will be inhibited as a result of a mutation introduced into the gene that encodes the proteins, i.e., a mutation in the rpoS and/or phoP genes.

BRIEF DESCRIPTION OF THE DRAWINGS

FIG. 2. Exemplary xenogeneic silencing proteins that can be used in the methods of the present invention. Genbank accession numbers are provided for identification purposes.

FIG. 3. Exemplary xenogeneic silencing proteins that can be used in the methods of the present invention. Genbank accession numbers are provided for identification purposes.

DETAILED DESCRIPTION OF ILLUSTRATIVE EMBODIMENTS

Figure 1:
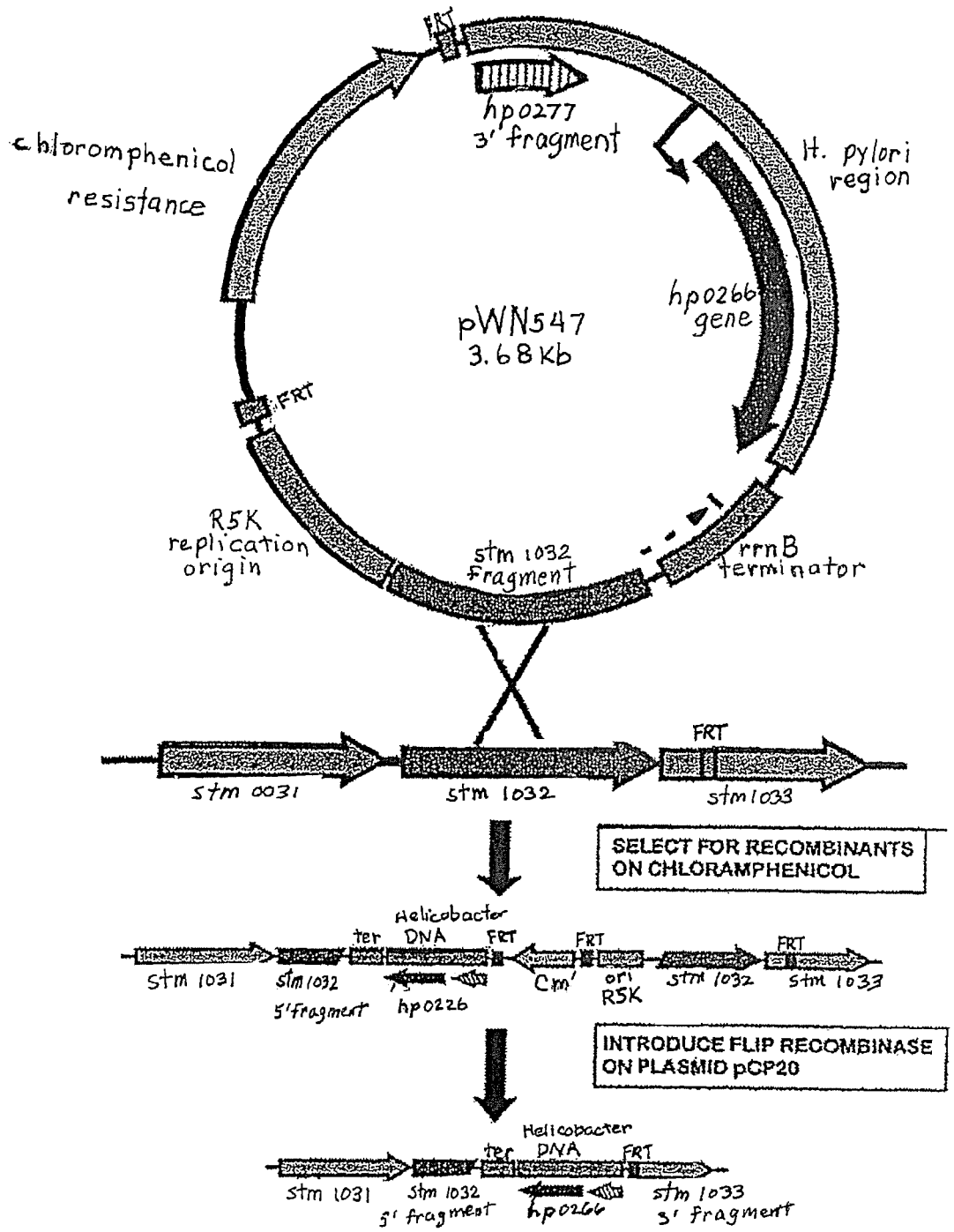
FIG. 1. A diagram of suicide vector pWN547 and its integration into the Salmonella chromosome to generate a strain of *Salmonella Typhimurium* containing the Helicobacter gene hp0226, its promoter and the 3' end of the adjacent hp0227 gene. Salient features of the plasmid are indicated. The thin black arrow upstream of hp0226 indicates the location of a putative promoter. The dashed thin black line above the rrnB terminator sequence designates the direction in which the terminator halts transcription.

The present invention is based, in part, on the discovery that bacteria possess a system to repress expression of foreign DNA sequences, and in particular, DNA sequences that are "AT rich".

DNA consists of four nucleotide bases: Guanine (G), Adenine (A), Thymidine (T) and Cytosine (C). On the DNA double helix, a G nucleotide base is always partnered with C, and a T nucleotide base is always partnered with an A. It has long been known that the DNA present in different species possesses unique "GC/AT-ratios." Human genes, for example, typically contain 65% AT basepairs (such genes are called "AT-rich") while the DNA of some bacteria have as few as 25% AT-basepairs ("GC-rich").

As used herein the term "xenogeneic silencing" refers to the process whereby bacteria repress expression from foreign DNA. Xenogeneic silencing proteins are polypeptides present in bacteria that act to repress expression from DNA sequences that are "AT-rich".

As used herein, the terms "polypeptide," "peptide" and "protein" are used interchangeably herein to refer to a polymer of at least about 6 amino acids.

As used herein the term "homolog" has its usual meaning in the art. The term generally refers to a nucleic acid or protein that has substantial sequence identity with respect to a reference sequence and, in the case of a protein, typically shares at least one activity with the reference sequence.

The term "ortholog" has its usual meaning in the art. The term generally refers to genes in different species that evolved from a common ancestral gene by speciation. Normally, orthologs retain the same function in the course of evolution. As used herein, the term "ortholog" refers to the protein products of the genes as well. "Paralogs" are genes related by duplication within a genome. Orthologs retain the same function in the course of evolution, whereas paralogs can evolve new functions, even if these are related to the original one. As used herein, the term "paralog" refers to the protein produces of the genes as well.

The present invention provides, inter alia, methods of "inhibiting the expression of at least one xenogeneic silencing protein". Inhibition of at least one xenogeneic silencing protein in a host cell is achieved, for example, when the expression and/or activity of the xenogeneic silencing protein is about 80%, optionally 50% or 25-0% as compared to a control. A control is a host cell having normal expression and/or activity levels of the xenogeneic silencing protein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB (Pearson and Lipman, 1988, *Proc. Natl. Acad. Sci. USA*, 85:2444-2448; Altschul et al., 1990, *J. Mol. Biol.* 215: 403410; Thompson et al., 1994, *Nucleic Acids Res.*, 22:4673-4680; Higgins et al., 1996, *Meth. Enzymol.* 266:383402; Altschul et al., 1993, *Nature Genetics*, 3:266-272; Brutlag et al., 1990, *Comp. App. Biosci.* 6:237-24), the disclosures of which are incorporated by reference in their entireties.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a cell" includes a combination of two or more cells, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the materials and methods are described herein.

The practice of this invention involves, inter alia, the construction of recombinant nucleic acids and the expression of genes in transformed bacterial cells. Molecular cloning techniques to achieve these ends are well known in the art. A wide variety of cloning and in vitro amplification methods suitable for the construction of recombinant nucleic acids, such as expression vectors, are well-known to persons of skill. Examples of these techniques and instructions sufficient to direct persons of skill through many cloning exercises can be found in Berger and Kimmel, Guide to Molecular Cloning Techniques, Methods in Enzymology volume 152 Academic Press, Inc., San Diego, Calif. (Berger); and Current Protocols in Molecular Biology, Ausubel, ed. John Wiley & Sons, Inc., New York, 1997.

Examples of protocols sufficient to direct persons of skill through in vitro amplification methods, including the polymerase chain reaction (PCR) the ligase chain reaction (LCR), Q.beta.-replicase amplification and other RNA polymerase mediated techniques can be found in Berger, Sambrook, and Ausubel, as well as Mullis et al. (1987) U.S. Pat. No. 4,683, 202; PCR Protocols A Guide to Methods and Applications (Innis et al. eds) Academic Press Inc. San Diego, Calif. (1990) (Innis); Arnheim and Levinson, *C&EN* 36-47, 1990; *The Journal Of NIH Research* 3: 81-94, 1991; Kwoh et al., *Proc. Natl. Acad. Sci. USA* 86: 1173, 1989; Guatelli et al., *Proc. Natl. Acad. Sci. USA* 87: 1874, 1990; Lomell et al., *J. Clin. Chem.* 35: 1826, 1989; Landegren et al., *Science* 241: 1077-1080, 1988; Van Brunt, *Biotechnology* 8: 291-294, 1990; Wu and Wallace, *Gene* 4: 560, 1989; and Barringer et al., *Gene* 89: 117, 1990. Improved methods of cloning in vitro amplified nucleic acids are described in Wallace et al., U.S. Pat. No. 5,426,039.

Expression cassettes for expressing recombinant genes in bacterial cells, such as *E. coli*, are also well known in the art as are vectors that include the expression cassettes, as well as fermentation protocols for using the expression cassettes to obtain expression of a heterologous polypeptide. As used herein, the term "expression vector" or "expression cassette" refers to any nucleic acid that can be introduced into a host cell or cell-free transcription and translation medium.

To obtain expression of a cloned gene, the expression cassettes can include, for example, sequences such as a promoter, ribosome binding sites for translational initiation, and transcription/translation terminator sequences. To allow selection of cells comprising the constructs, one or more selectable marker genes (e.g., antibiotic-resistance genes) can be included in the expression vectors. The vectors can comprise other sequences to allow the vector to be cloned in prokaryotic hosts, such as a broad host range prokaryote origin of replication. One of skill will recognize that each of these vector components can be modified without substantially affecting their function.

The expression vectors typically contain a transcription unit or expression cassette that contains all the elements required for the expression of the DNA encoding the polypeptide in the host cells. A typical expression cassette comprises, for example, a promoter linked to the DNA sequence encoding a polypeptide of interest and a ribosome binding site. The promoter is preferably positioned about the same distance from the heterologous transcription start site as it is from the transcription start site in its natural setting. As is known in the art, however, some variation in this distance can be accommodated without loss of promoter function. In addition to a promoter sequence, the expression cassette can also contain a transcription termination region downstream of the structural gene to provide for efficient termination. The termination region can be obtained from the same gene as the promoter sequence or can be obtained from a different gene. Commonly used prokaryotic control sequences, which are defined herein to include promoters for transcription initiation, optionally with an operator, along with ribosome binding site sequences, include such commonly used promoters as the T7 promoter system, the beta-lactamase (penicillins) and lactose (lac) promoter systems including the hybrid trp-lac promoter (Change et al., *Nature* 198: 1056, 1977; Amann et al., *Gene* 25: 167, 1983; de Boer et al., *Proc. Natl. Acad. Sci. USA* 80: 21, 1983), the tryptophan (trp) promoter system (Goeddel et al., *Nucleic Acids Res.* 8: 4057, 1980), and the lambda-derived $P_L$ promoter and N-gene ribosome binding site (Shimatake et al., *Nature* 292: 128, 1981). Any available promoter system that functions in prokaryotes can be used, including constitutive or regulated promoters.

The vectors can also contain a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria.

The vectors can also comprise selectable marker genes to allow selection of bacterial cells bearing the desired construct. These genes encode a polypeptide necessary for the survival or growth of transformed host cells grown in a selective culture medium. Host cells not transformed with the vector containing the selection gene will not survive in the culture medium. Typical selection genes encode polypeptides that confer resistance to antibiotics or other toxins, such as ampicillin, neomycin, kanamycin, chloramphenicol, or tetracycline. Selectable markers can encode polypeptides that complement auxotrophic deficiencies or supply critical nutrients not available from complex media, e.g., the gene encoding D-alanine racemase for Bacilli. A number of selectable markers are known to those of skill in the art and are described for instance in Sambrook et al., supra.

Construction of suitable vectors containing one or more of the above listed components can employ standard ligation techniques. Isolated plasmids or DNA fragments can be cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods.

A number of bacterial host cells can be used with the vectors of the invention. Examples of useful bacteria include *Escherichia, Enterobacter, Azotobacter, Erwinia, Bacillus, Pseudomonas, Bordetella, Rhodobacter, Klebsielia, Proteus, Salmonella, Serratia, Shigella, Rhizobium, Vitreoscilla,* and *Paracoccus*. Depending on the host cell used, transformation is done using standard techniques appropriate to such cells. Suitable techniques include, for example, calcium treatment employing calcium chloride, polyethylene glycol, or electroporation.

The present invention provides methods of inhibiting the expression of at least one xenogeneic silencing protein that is endogenous to a host cell and culturing the host cell under conditions that allow for the expression of a foreign polypeptide. The xenogeneic silencing proteins of the present invention can be any protein that acts to repress foreign DNA sequences in a host cell. DNA binding proteins and proteins that interact with DNA binding proteins are examples of xenogeneic silencing proteins that can be used in the present invention. Without being bound by theory, it is believed that the xenogeneic silencing proteins that act as DNA binding proteins bind to foreign DNA that is AT rich thereby preventing the DNA from being activated.

An exemplary xenogeneic silencing protein for use in the present invention is H-NS. H-NS is a histone-like nucleoid structuring polypeptide encoded by the hns gene. H-NS belongs to a family of small abundant nucleoid associated proteins of bacteria that have the ability to bind to DNA with relatively low sequence specificity. H-NS is able to recognize newly encountered DNA that is more AT-rich that the rest of the bacterial genome (Navarre et al., *Science* 313: 236-238, 2006). Without being bound by theory, it is believed that AT-rich foreign DNA becomes coated with H-NS which prevents the DNA from being transcribed. In this manner, bacteria can determine whether a piece of encountered DNA is foreign and prevent such sequences from being transcribed.

An exemplary paralog to H-NS for use in the present invention is the StpA protein. The StpA protein is a paralog of H-NS that also acts as a DNA binding polypeptide (Free et al., *Journal of Bacteriology* 180: 994-997, 1998).

Proteins that interact, directly or indirectly, with DNA binding proteins and homologs of such proteins can be used in the present invention as xenogeneic silencing proteins. The H-NS protein interacts with the Hha protein in *E Coli* and the Hha protein has been proposed to be an independent oligomerization domain of H-NS. (Nieto et al., *Journal of Bacteriology* 184: 629-635, 2002). YdgT is a Hha paralog that that has been shown to form heteromeric complexes with H-NS and StpA (Paytubi et al., *Molecular Microbiology* 54: 251-263, 2004) and can also be used in the methods of the present invention.

Accordingly, the inhibition of the expression of at least one of the H-NS protein, StpA protein, Hha protein, and YdgT protein or any combination thereof can be used in the present invention to increase expression of foreign DNA in a host cell. In certain embodiments, wherein at least one of the H-NS protein, StpA protein, Hha protein, and YdgT protein or any combination thereof are inhibited, the host cell will be *E coli*. Although *E. coli* is one example of a bacterial host cell used commonly to express foreign polypeptide, other bacterial host cells can be used in the present invention to express foreign DNA, including for example, *Escherichia, Enterobacter, Azotobacter, Erwinia, Bacillus, Pseudomonas, Bordetella, Rhodobacter, Xyella, Klebsielia, Proteus, Salmonella, Serratia, Shigella, Rhizobium, Vitreoscilla*, and *Paracoccus*.

Additional xenogenic silencing proteins that can be used in the present invention include for example, the XrvA, BpH3, BbH3, HbsU, AbrB, MvaT, and MvaU proteins.

In certain embodiments of the present invention, the bacterial host cell will be *Xylella* or *Xanthomonas* and the xenogeneic binding protein will be a XrvA polypeptide and/or polypeptide that interacts with the XrvA polypeptide. In certain embodiments, the bacterial host cell will be *Bordetella* and the xenogeneic binding protein will be a BpH3 and/or BbH3 polypeptide and/or polypeptide that interacts with the BpH3 and/or BbH3 polypeptide. In certain embodiments, the bacterial host cell will be *Rhodobacter* and the xenogeneic binding protein will be a HvrA polypeptide and/or polypeptide that interacts with the HvrA polypeptide. In certain embodiments, the bacterial host cell will be *Pseudomonas*, e.g., *Pseudomonas aeruginosa*, and the xenogeneic binding protein will be a MvaT DNA binding polypeptide or a polypeptide that interacts with the MvaT DNA binding polypeptide, such as the MvaU polypeptide (Vallet-Gely et al., PNAS 102: 11082-11087, 2005). In certain embodiments, the bacterial host cell will be *Yersinia enterocolitica* and the xenogeneic binding protein will be *Yersinia enterocolitica* H-NS or YmoA polypeptide (Nieto et al., *Journal of Bacteriology* 184: 629-635, 2002). In certain embodiments, the host cell will be *Salmonella* and the DNA binding polypeptide will be H-NS. In certain aspects, the xenogeneic silencing protein in host cells other than *E coli* will be an HNS-like polypeptide.

Any H-NS related or H-NS-like protein, including homologues of H-NS, i.e., paralogs and orthologs, that acts to repress foreign DNA sequences in a host cell can be used in the present invention as xenogeneic silencing proteins. Generally, the HNS related proteins will be able to at least partially restore the wild-type phenotype in *E coli* hns mutants. A review of the H-NS and H-NS like proteins is provided in Tendeng and Bertin, *Trends in Microbiology* 11(11): 511-518, 2003). The H-NS related proteins are believed to be organized into two modules separated by flexible linkers. They are believed to oligomerize using their N-terminal and to bind DNA by the C-terminal domain. The C-terminal domain of the H-NS related proteins is a conserved region.

In certain embodiments, H-NS or H-NS like proteins of the present invention will have substantial homology, e.g., about 70%, about 75%, about 80%, about 85%, about 90%, about 92%, about 95% or 100% homology, to the following consensus sequence Y-x(6)-[G or S]-[E or D]-x(0,2)-T-W-[T or S]-G-[Q or R]-G-[R or K]-x-P-x(4,5)-A-x(3,4)-G (SEQ ID NO:1) where "x" represents any amino acid, and the bracketed number beside "x" represents the number of "x"s present. For example x(0,2) refers to either zero "x"s or 2 "x"s.

FIGS. 2 and 3 provide exemplary xenogeneic silencing proteins that can be used in the methods of the present invention. Genbank accession numbers are provided for identification purposes. In certain embodiments, the xenogeneic silencing proteins will not have the exact sequence but a sequence substantially identical to the one referenced by the accession number.

The methods of the present invention, inter alia, comprise the steps of inhibiting the expression of a xenogeneic silencing protein that is endogenous to the host cell. In certain embodiments wherein the inhibition of xenogeneic silencing protein causes detrimental effects to the host cell, it will be preferably to suppress the detrimental effects by introducing further mutations into the cell. The mutations can be spontaneous arising mutations or engineered mutations. Accordingly, in certain embodiments, the methods of the present invention will include a step of introducing a second site mutation into the host cell. The second site mutation can be at a site other than the hns gene.

An exemplary second site mutation is one that inhibits the expression of an alternative sigma factor $\sigma^S$ protein or an alternative sigma factor $\sigma^S$ dependent protein. Alternative sigma factor $\sigma^S$ dependent proteins include, for example, the CsgBA, HhdeAB, Mcc (microcin C51) and OsmY proteins (Barth et al., *Journal of Bacteriology* 177: 3455-3464, 1995). Any method of inhibiting the expression of an alternative sigma factor $\sigma^S$ protein or an alternative sigma factor $\sigma^S$ dependent protein can be used herein. For example, a mutation can be introduced into the rpoS gene that encodes the alternative sigma factor $\sigma^S$ protein.

Another exemplary second site mutation is one that inhibits the expression of the virulence gene regulator polypeptide, PhoP. Any method of inhibiting the expression of the virulence gene regulator polypeptide, PhoP, can be used herein. For example, a mutation can be introduced into the phoP gene that encodes the virulence gene regulator polypeptide, PhoP.

In certain embodiments of the present invention, the bacterial host cell will have a mutation in at least one of the hns, rpoS, and phoP coding sequences. In certain embodiments, the bacterial host will have a mutation in the hns and rpoS coding sequences, in the hns and phoP coding sequences, or in the hns, rpoS and phoP coding sequences.

The present invention provides host cells having inhibited expression of a xenogenic silencing protein. In certain embodiments, expression of the protein is affected by mutating the gene that encodes the xenogeneic silencing polypeptide, using standard recombinant techniques. For example, in certain embodiments, homologous or non-homologous recombination can be used to delete, disrupt, or alter a gene. The disruption of the gene will be such that it adversely affects the normal, wild-type gene product within the same cell, i.e., expression of the active polypeptide is inhibited.

For example, in certain aspects, the present invention provides a recombinant bacterial host cell in which the hns gene has been deleted or disrupted by homologous recombination using a recombinant DNA vector. This host cell, disrupted in its ability to make the wild type hns gene product at all or in sufficient quantities is inhibited in its ability to repress expression of foreign genes.

Expression vectors can be used to create the deletion mutants of the present invention. Those of skill will also recognize that standard recombinant techniques can be used to construct host cells in which one or more genes involved in xenogeneic silencing is rendered inactive or inhibited it is ability to make its protein product. Thus, the invention provides such host cells, which are exemplary host cells for expressing recombinant polypeptides. Exemplary host cells of this type include those in which one or more of any of the hns genes, hns homolog genes and H-NS interacting polypeptide encoding genes has been disrupted. Such host cells can be constructed by a process involving homologous recombination using a vector that contains DNA homologous to the regions flanking the gene segment to be altered and positioned so that the desired homologous double crossover recombination event desired will occur.

Methods of constructing mutations in the hns gene and determining whether the mutations are sufficient to inhibit H-NS polypeptide activity are known in the art. For example, hns-205::Tn10 is a well-characterized allele which harbors a Tn10 insertion in codon 93 of hns and produces both a truncated hns mRNA species and a truncated N-terminal polypeptide fragment. (Barth et al. supra) The hns2 deletion carries about a 750 base pair insertion within the first 22 codons of the hns open reading frame (Barth et al. supra). Another exemplary mutation is the deletion of the region from 90 bp upstream of the hns ATG start codon to 259 bp within the hns coding region Methods of constructing deletions in the rpoS gene and/or phoP gene are also known in the art and not described herein in detail. Exemplary bacterial strains and mutations therein for use in the present invention include, for example, F$^-$Δ(arg-lac)U169 araD139 rpsL150 ptsF25 flbB5301 rpsR deoC relA1; MC4100 rpoS 359::Tn10; MC4100 Φ(proU::lacZ) hyb2(∠placMu15) hns-205::Tn10; MC4100 Φ(hns::lacZ)1 hns-206::Ap$^r$; MC4100 hns-205::Tn10; MC4100 hns-206:: Ap$^r$; MC4100 hns-206::Ap$^r$ rpoS359::Tn10; MC4100 Φ(csi-5::lacZ)(λplacMu55); RO151 rpoS359::Tn10; RO151 hns-206::Ap$^r$; RO151 hns-206::Ap$^r$ rpoS359::Tn10; MC4100 Φ(csiD::lacZ)(λplacMu15); DW12 rpoS359::Tn10; DW12 hns-206::Ap$^r$; DW12 hns-206::Ap$^r$ rpoS359::Tn10; MC4100 Φ(csiE::lacZ)(λplacMu15); DW16 rpoS359::Tn10; DW16 hns-206::Ap$^r$; DW16 hns-206::Ap$^r$ rpoS359::Tn10; MC4100 (λMAV103: bolA$_{p1}$::lacZYA Kan$^r$); RH95 rpoS359::Tn10; RH95 hns-206::Ap$^r$; RH95 hns-206::Ap$^r$ rpoS359::Tn10; MC4100 Φ(otsA::lacZ)7(λplacMu55); FF2032 rpoS359:: Tn10; FF2032 hns-206::Ap$^r$; FF2032 hns-206::Ap$^r$ rpoS359::Tn10; MC4100 (λRZ5: rpoS742::lacZ); RO200 hns-205::Tn10; MC4100 [λRZ5: rpoS742::lacZ(hyb)]; RO91 hns-205::Tn10; MC4100 [λRS45: rpoS742::lacZ (hyb)]; and RH159 hns-206::Ap$^r$; MC4100 zfi3251::Tn10$^a$. (Barth et al. supra)

Although the use of deletion mutants is one method of inhibiting the expression and activity of the xenogeneic silencing proteins, any other method for inhibiting the expression and/or activity of a gene and/or protein in a host cell can be used in the methods of the present invention. For example, expression of the xenogeneic silencing genes can be specifically suppressed at the molecular level by utilizing antisense nucleic acids. In brief, traditional methods of gene suppression, employing anti-sense RNA or DNA, operate by binding to the reverse sequence of a gene of interest such that binding interferes with subsequent cellular processes and blocks synthesis of the corresponding polypeptide.

Overexpression of a small RNA, Rcd, encoded by the plasmid ColE1 in hns mutant bacterial cells has been shown to block cell division and growth in the bacterial cells and drive cells into a quiescent state (see U.S. Pat. No. 6,190,867 and Rowe and Summers, *Applied and Environmental Microbiology* 65: 2710-2715, 1999). For use herein, the term a quiescent cell refers to a cell that has been induced into a quiescent state by overexpression of the Rcd RNA. The host cells of the present invention have not been induced into quiescence by over expression of the Rcd RNA. Accordingly, the host cells of the present invention can be characterized as non-quiescent cells and/or as cells having no expression or basal expression levels of an rcd gene. It will be understood that host cells of the present invention are capable of progressing through the cell cycle and are capable of cell growth.

The present invention provides, inter alia, methods and host cells for the expression of a polypeptide in a bacterial host cell. In certain exemplary embodiments, the polypeptide will be a therapeutically useful polypeptide. The polypeptide can be, for example, a therapeutic protein, developed for administration to a subject. Accordingly, the polypeptide can be useful in the treatment of diseases and conditions, including, for example, arthritis, immune and inflammatory disorders, cancer, Alzheimer's disease, heart disease, diabetes, multiple sclerosis, hepatitis, and AIDS. Therapeutic proteins that can be expressed using the present methods include, for example, etanercept, insulin, erythropoietin (e.g., erythropoietin alpha, erythropoietin beta), interferon (e.g., interferon gamma 1b, interferon alfa-2b, interferon alfa-2a, interferon beta-1a, interferon alfacon-1), G-CSF, interleukin (e.g., interleukin-2), somatotropin, glucagon, Factor VIII, GM-CSF, tissue plasminogen activator, tumor necrosis factor alpha-1a, or caspase-1.

EXEMPLARY EMBODIMENTS

Example 1

Silencing of Foreign DNA with Low GC Content by the H-NS Protein in *Salmonella*

A derivative of *Salmonella enterica* serovar Typhimurium strain ATCC 14028s containing an in-frame 15 nucleotide deletion in the rpoS gene was used in these studies (rpoS$^{low}$). This mutation results in the deletion of residues 61 thru 65(YLGEI) (SEQ ID NO:2) of the σ$^s$ protein resulting in a reduction in σ$^s$ activity. To generate an hns mutation, the region from 90 bp upstream of the hns ATG start to 259 bp within the hns coding region was replaced by the kanamycin-resistance cassette of plasmid pKD4 using the lambda-red recombinase method (Datsenko and Wanner, Proc Natl Acad Sci USA 97: 6640-5, 2000) using primers of sequence (5'-GAGATAATTAAAACGTGTGCT-TAATAAAGCGTAATTTTGAGTGTAGGCTGGAGCTGC TTC) (SEQ ID NO:3) and (5'-ACATAGCTATATTTAGCCG-GACGAGCTGCGCGTTTAGCTTCATAT-GAATATCCTCCTT AG) (SEQ ID NO:4). To generate the plasmids used for the ChIP-on-chip analysis the hns gene and 830 bp of 5' upstream sequence was PCR amplified from wild-type *Salmonella* strain 14028s using Pfu polymerase and primers of sequence (5'-TTGGATCCGACGACAAAC- CGATACGAGAG) (SEQ ID NO:5) and (5-TTAT-TAAAGCTTGGCTGCAGATTCCTTGAT-CAGGAAATCTTCCAGTTGC) (SEQ ID NO:6). The resulting product was digested with BamHI and HindIII enzymes and ligated into the respective BamHI and HindIII sites of low copy plasmid pHSG76(Takeshita et al.,*Gene* 61: 63-74, 1987). The resulting plasmid was digested with PstI and HindIII enzymes prior to religation with linkers to create in-frame extensions of the carboxy-terminus of the H-NS protein with either a FLAG epitope (ADYKDDDDK*) (SEQ ID NO:7), to generate pWN425 or HA epitope (ADYPYD-VPDYA*) (SEQ ID NO:8) to generate pWN426.

Construction of the hp0226 containing strains was performed by single-crossover recombination of a suicide vector containing a fragment of *Salmonella* chromosome (nucleotides 120165 to 1120695 of the published *Salmonella* LT2 genome), the *E. coli* rrnB terminator sequence, and the hp0226 gene and upstream region (corresponding to nucleotides 233929 to 235827 of the published genome sequence of *H. pylori* strain 26695; hp0226 clone DNA gift of Dr. Nina Salama).

The suicide vector used in this study was constructed by altering plasmid pKD3, a chloramphenicol and ampicillin resistant vector with an R6K origin of replication requiring the pir protein in trans for replication that also contains a transcription terminator from the *E. coli* rrnB gene (Datsenko and Wanner, Proc Natl Acad Sci USA 97: 6640-5, 2000). The chloramphenicol acetyltransferase gene on this plasmid is flanked by FRT (Flip recombinase target) sites to facilitate removal of the cassette with Flip recombinase (Datsenko and Wanner, *Proc Natl Acad Sci U S A* 97: 6640-5, 2000). All manipulations of this vector were performed in *E. coli* strains encoding the pir protein like SM10($\lambda$pir). Briefly, pKD3 was PCR amplified with primers (5'-AAAGGATC-CCCGAAAAGTGCCACCTG) (SEQ ID NO:9) and (5'-AAAGGATCCGCAAGATCCGCAGTTCAACC) (SEQ ID NO:10), restriction digested with BamHI and relegated to generate pWN523(thereby replacing the beta-lactamase gene of pKD3 with a BamHI site). *Salmonella* genomic DNA was PCR amplified with primers of sequence (5'-TATAGATCTC-CAACCTGGAGTCTTTCCGTATG) (SEQ ID NO:11) and (5'-TATAGATCTCATTTTTATCGCCGCCACTG) (SEQ ID NO:12) to obtain a 530 bp fragment of genomic DNA corresponding to the 3' end of stm1032. Digestion of this fragment with BglII and ligation into BamHI-digested pWN523 yielded pWN524(note the BglII and BamHI sites were destroyed by this ligation). pWN524 was subsequently PCR amplified with primers of sequence (5'-AAGGATCCTACA-CAATCGCTCAAGAC) (SEQ ID NO: 13) and (5'-AAAG-GATCCCGGGAATTCGTGTAGGCTGGAGCTGCTTC) (SEQ ID NO:14) and digested with BamHI to yield plasmid pWN525(inserted recognition sites for EcoRI, SmaI, BamHI restriction enzymes downstream of the rrnB terminator). The fragment of *H. pylori* DNA encoding hp0226, its promoter, and the 3' end of hp0227 was inserted into the BamHI site of pWN525 to generate pWN547.

To generate the hp0226 containing strains, plasmid pWN547 was electroporated into a *Salmonella* strain engineered with a single FRT site in the STM1033 gene and single crossover recombinants were selected for chloramphenicol resistance and verified by PCR. This region of the chromosome was subsequently transferred to the rpoS$^{low}$ strain via P22 transduction using phage P22 HT105/1 int-201 and selection on chloramphenicol. Removal of the chloramphenicol cassette, R6K origin and duplicated stm1032 sequence was achieved by introducing the Flip recombinase in trans on the plasmid pCP20. In this manner a region encompassing the 3' end of stm1032 and the 5' end of stm1033(nucleotides 1120696 to 1121129 of the published *Salmonella* strain LT2 genomic sequence) was replaced with the *E. coli* rrnB terminator, the *H. pylori* sequence and a single FRT site to generate strain WN552. The hns gene of this strain was subsequently replaced with hns::kan (see above) by P22 transduction to generate strain WN555. Introduction of plasmids pWN425 or pWN426 into strain WN555 complemented the hns mutation and generated strains WN558 and WN559, respectively.

ChIP-on-Chip Determination of H-NS Binding Regions.

Chromatin immunoprecipitation was carried out. Briefly, the rpoS$^{low}$ hns mutant strains complemented with either pWN425 (pHNS-FLAG) or pWN426(pHNS-HA) were grown in N-minimal medium containing 10 mM MgSO4 overnight with chloramphenicol (10.mu.g/m1). Overnight cultures were subcultured 1:200 in fresh N-minimal medium and grown to mid-logarithmic phase (OD600=0.4). To crosslink protein to DNA, formaldehyde was added to a final concentration of 1% for 15 min at room temperature before quenching with 1.25 mM glycine for 10 min Cells were washed twice with cold PBS and sonicated extensively to generate chromosomal fragments of average size .about.700 bp. Lysates were cleared by centrifugation and precipitated with anti-HA antibody (clone HA-7; Sigma) using agarose protein G beads (Calbiochem). In this experimental setup, the H-NS protein tagged with the FLAG epitope served as a negative control as it does not interact with the HA antibody.

Both experimental and control precipitates obtained from 20 ml of cells were reciprocally labeled twice following the protocol for genomic DNA, hybridized to arrays and scanned as described (Porwollik et al., J Bacteriol 186: 5883-98, 2004). Thresholds for significance were considered as follows: A>10, M>1.5, and p<0.005. Both experimental and control precipitates obtained from 20 ml of cells were reciprocally labeled twice following the protocol for genomic DNA, hybridized to arrays and scanned.

The high resolution arrays used for the ChIP-on-chip analysis were synthesized by NimbleGen to contain 387,000 46.about.50-mer oligos, including 377,230 *Salmonella* probes that each hit genome at a unique position. The probes were designed based on *S. Typhimurium* LT2 genome (NC_003197), with a moving window of about 12 bases. The probes located in the three LT2 regions not present in the genome of the 14028s strain (Fels-1, Fels-2 and STM3255-3260) were removed from further analysis. Two NimbleGen arrays were hybridized with genomic DNA and has-bound DNA from a chromatin immunoprecipitation with a dye swap. Oligos exhibiting weak (raw intensity less than 4000) and saturated (raw intensity greater than 40000) signals in the control (genomic DNA) sample were excluded from analysis. Raw intensities were normalized by the median intensity in each channel and the ratios were calculated by log base 2 (hns-bound DNA/genomic DNA) after the normalization. Two arrays were scale normalized to scale the log-ratios to have the same median-absolute-deviation (MAD) across arrays.

Analysis of hp0226 Expression and H-NS Binding.

To analyze transcript levels of hp0226, total RNA was prepared from log phase cultures (OD600 =1.0) of strains WN552 (wild-type, hp0226 strain) and WN555 (hns mutant, hp0226 strain) grown in Luria broth (LB). Quantitative PCR and subsequent analysis were performed essentially as described (Navarre et al., *Mol Microbiol* 56: 492-508, 2005). Primers to amplify hp0226 were of sequence (5'-TAAAGGT-GTAGCACACCACCACCA) (SEQ ID NO:15) and (5'-TTTGAGAGAAGGC TCATTTGCCGC) (SEQ ID NO:16). Primers to amplify proV, an H-NS regulated gene used as a positive control, were of sequence (5'-TCAGGTG-GATTTTTGCTGGTTG) (SEQ ID NO:17) and (5'-TAT-TGCGAGGTGCTATCGGCTGTG) (SEQ ID NO:18). Primers to amplify marA, a non-H-NS dependent gene used as a negative control, were of sequence (5'-TTGAACGTC-CGGGTCAATGTTTGC) (SEQ ID NO:19) and (5'-TATTC-CAAATGGCACCTGCA ACGG) (SEQ ID NO:20). Primers to amplify gyrB, a housekeeping gene not significantly affected by H-NS under these conditions, were of sequence (5'-GATGGGTTTTCCAGCAGGTATTC) (SEQ ID NO:21) and (5'-AGGTCTGATTGCGGTGGTTTC) (SEQ ID NO:22). Equivalent amounts of RNA were loaded for each sample tested and small variations in gyrB were used to normalize expression levels between samples.

To measure the degree of H-NS binding to hp0226, strains WN558 and WN559 were formaldehyde-crosslinked as described above and chromosomal DNA was sheared by sonication to fragments ranging in size between ~300-600 by (average size of ~450 bp was determined by agarose gel electrophoresis of DNA after crosslinks were removed by heat treatment). DNA-protein complexes were immunoprecipitated with anti-HA antibody, decrosslinked, and purified as described above with DNA from WN558(FLAG-tagged HNS) serving as a negative control. Relative enrichment of the hp0226, proV, marA and stm1033 sequences were determined by comparing relative copies of each gene in total chromosomal DNA (where the copies of all genes are equivalent) to recovered DNA (where only certain genes were recovered due to their interaction with H-NS) by Q-PCR. marA was used as a reference sample for no H-NS interaction and "fold enrichment" was determined to be the amount of each gene recovered in comparison to the marA sample (e.g., 53.6 copies of proV DNA were recovered after immunoprecipitation for each copy of the marA gene). Several factors affect the apparent level of recovery including the amount of protein bound at any given site (more efficient immunoprecipitation of DNA segments bound by multiple copies of tagged protein is assumed) and the distance of the primer set from the location of the binding site (i.e., the DNA was sheared into 300-600 bp fragments; therefore a primer set located more than 600 bp away will be less likely to amplify a gene after immunoprecipitation than a primer set 100 bp from the site). The primer set used to amplify stm1033 was 5'-TGCAGGAAGAACAGCGTAACCGTA (SEQ ID NO:23) and 5'-TCGGCGT AATACCTTTCGCCATCT) (SEQ ID NO:24).

To determine the *Salmonella* genes controlled by H-NS, construction of an hns null mutation was attempted in *Salmonella enterica* sv. *Typhimurium* (*S. Typhimurium*). hns mutant strains were found to be non-viable unless additional mutations were present in either rpoS encoding the alternative sigma factor as (p32) or phoP encoding the virulence gene regulator PhoP. These mutants could tolerate an hns mutation but exhibited a reduced growth rate, while an hns mutation in an rpoS phoP double mutant background displayed growth similar to that of wild type.

The lethality of the hns mutation is suppressed by compensatory mutations in phoP or rpoS in *Salmonella Typhimurium*. A targeted replacement was made in the hns gene of *S. Typhimurium* strain 14028s rpoSΔ61-65 (rpoS$^{low}$, encoding an in-frame deletion of residues 61-65 (YLGEI) from the mature $\sigma^s$ protein) with a kanamycin resistance cassette (aph) from pKD4. The hns::aph mutation was subsequently transduced via P22 transduction using phage P22HT105/1 int-201 into the wild-type *S. Typhimurium* strain 14028s or a strain containing mutations in rpoS or phoP. Growth of kanamycin resistance colonies was monitored on LB plates containing 50µg/ml kanamycin. As a control to show that inherent growth differences between strains was minimal under these conditions, another kanamycin resistance cassette (an interruption of the rcsA gene) was transduced in parallel. Wild-type *Salmonella* transduced with hns::aph generated microcolonies failed to grow after passage, whereas both phoP:: Tn10dCm and rpoS mutant strains transduced with hns:: aph were able to grow, albeit more slowly than strains transduced with rcsA::aph. The rpoS$^{low}$ phoP::Tn10dCm hns triple mutant grew at a rate similar to that of the rcsA::aph strains, although colonies were mucoid in appearance.

This suggests the detrimental effect of an hns mutation is due to derepression of one or more $\sigma^s$ and PhoP-activated loci and might explain why hns mutations are not lethal in some laboratory strains, as rpoS mutant alleles are commonly acquired after laboratory passage (Ferenci, Trends Microbiol 11: 457, 2003). To enable studies of H-NS function in *Salmonella*, an hns mutation in *S. Typhimurium* carrying a spontaneous rpoS mutation that confers diminished $\sigma^s$ activity was constructed.

*Salmonella* genes regulated by H-NS were identified by comparing transcript levels in hns+ and hns− strains by cDNA microarray analysis. Of 4,529 open reading frames (ORFs) represented on the array (4,422 from the chromosome and 107 from the virulence plasmid), transcript levels of 178 ORFs were reduced by greater than three-fold, while 409 transcripts were more abundant in the hns mutant. As previously reported for *E. coli*, many H-NS "activated" genes are involved in chemotaxis and motility (Hromockyj et al., *Mol Microbiol* 6: 2113, 1992). Among genes repressed by H-NS are many known virulence loci of *Salmonella* including the pathogenicity islands SPI-2, SPI-3, and SPI-5, most characterized virulence islets, and the plasmid spv genes.

A large number of H-NS repressed genes bear the hallmarks of acquisition from a foreign source, i.e. are not universally present in the genomes of closely related enteric bacteria and possess significantly reduced GC-content compared to the resident genome (McClelland et al., *Nature* 413: 852, 2001). Of 409 ORFs exhibiting repression by H-NS, only 40 (9.8%) are common to all reference genomes whereas 265 (64.7%) are found exclusively in *Salmonella*. Most H-NS repressed genes have GC content lower than the overall genome: the average GC-content of an ORF displaying 3-fold or greater repression by H-NS is 46.8% whereas the average GC content of the entire *Salmonella* LT2 genome is 52.2%.

Microarray analysis of cDNA provides only indirect evidence that a transcription factor interacts directly with a given sequence, as many regulatory interactions are dependent on a cascade of transcription events. For example, the apparent activation of flagellar genes by H-NS most likely occurs via H-NS mediated repression of HdfR, a repressor of the flagellar regulators FlhDC (Dorman, *Nat Rev Microbiol* 2: 391, 2004). *Salmonella* genes that interact directly with H-NS were therefore determined by chromatin immunoprecipitation of in vivo crosslinked H-NS/DNA complexes followed by microarray (ChIP-on-chip) analysis on either a custom ORF array or a tiled oligonucleotide array with 385,000 features (NimbleGen, Madison Wis.; Materials and Methods are available as supporting material on *Science* online).

Of the 4,438 chromosomal genes covered in the ORF array, 745 (16%) co-immunoprecipitated with H-NS. A striking correlation was observed between H-NS binding predicted in silico by low GC-content and binding measured experimentally by chromatin immunoprecipitation. Only 5 of 745 precipitated sequences (0.7%) were not situated within 1000 nucleotides of a chromosomal region displaying average GC content <49% (averaged over a 1000 nt span). Of 615 ORFs in the annotated *Salmonella* genome with GC content <47%, 433(70.4%) co-precipitated with H-NS. The oligonucleotide array provided detailed resolution of H-NS binding sites and revealed a strong correlation between H-NS binding and regional AT-content whether or not the site was in a promoter (see FIG. 1). Some horizontally transferred sequences (notably SPI-1 and SPI-4) in which cDNA microarray analysis demonstrated only slight transcriptional repression were found to interact directly with H-NS, suggesting either that H-NS binding is not an effective silencer at all binding sites, or that conditions employed during the cDNA analysis did not favor expression or silencing of these genes.

To prospectively test whether H-NS is capable of targeting AT-rich DNA from a foreign source, a gene from *Helicobacter pylori* (hp0226, % GC=39.7) was recombined along with its promoter into a non-essential region of the *Salmonella* chromosome with a uniform average GC-content >50% and no demonstrable interaction with H-NS. Chromatin immunoprecipitation with quantitative PCR (ChIP/Q-PCR) revealed significant association of H-NS with hp0226 but not with the adjacent gene stm1033 (% GC=52.5). Reverse transcriptase/Q-PCR measurement of transcript levels revealed significantly higher (>15-fold) hp0226 expression in the hns mutant compared to wild-type. It can be concluded that AT-rich content per se is sufficient for H-NS mediated silencing and that H-NS can target AT-rich sequences irrespective of chromosomal location.

These findings provide a role for H-NS in recognizing AT-rich sequences as foreign and preventing their expression. Such "xenogenetic silencing" can protect the cell from detrimental consequences of invading DNA. An association has been noted between H-NS and some horizontally transferred genes in pathogenic *E. coli* (Yang et al., *Microbiology* 151: 1199, 2005; Beltrametti et al., *J Bacteriol* 181: 3409, 1999; Westermark et al., *J Bacteriol* 182: 6347, 2000; Bustamante et al., *Mol Microbiol* 39: 664, 2001), *Shigella* spp. (Dorman et al., *Int J Med Microbiol* 291: 89, 2001; Beloin and Dorman, *Mol Microbiol* 47: 825, 2003), *Vibrio cholerae* (Krishnan et al., *Infect Immun* 72: 3961, 2004), *Proteus mirabilis* (Coker et al., *J Bacteriol* 182: 2649, 2000), *Yersinia* spp. (Heroven et al., *Mol Microbiol* 53: 871, 2004) and *Erwinia* chrysanthemi (Nasser and Reverchon, *Mol Microbiol* 43: 733, 2002), but not satisfactorily explained (Dorman, *Nat Rev Microbiol* 2: 391, 2004). A number of virulence regulators (e.g., SlyA (Wybom et al., *J Bacteriol* 186: 1620, 2004), RovA (Heroven et al., *Mol Microbiol* 53: 871, 2004), Ler (Haack et al., *Infect Immun* 71: 384, 2003), CRP-PapB (Forsman et al., *Proc Natl Acad Sci USA* 89: 9880, 1992), and ToxT (Yu and DiRita, *Mol Microbiol* 43: 119, 2002)) act as anti-silencers by displacing H-NS at specific promoters. A model in which H-NS exploits low GC-content to silence horizontally acquired sequences provides a unifying explanation for these disparate observations across several bacterial species. The evolutionary development of selective counter-silencing mechanisms provides a means by which an organism is protected from adverse consequences of foreign DNA but can nevertheless selectively activate individual loci that confer a fitness advantage.

This model provides a bacterial analogue to the silencing of transposons and mobile genetic elements by heterochromatin/RNAi in eukaryotes (Zilberman and Henikoff, *Genome Biol* 5: 249, 2004). Like heterochromatin, H-NS appears both to function as a silencer of potentially harmful sequences and to exert control over local nucleoid structure. However, whereas histones are highly conserved among eukaryotes, the primary sequence of H-NS is poorly conserved among bacteria outside of the Enterobacteriaceae (Bertin et al., *Mol Microbiol* 31: 319, 1999). Furthermore, the almost exclusive restriction of H-NS binding to AT-rich regions and the maintenance of nucleoid domain structure despite the absence of H-NS (Brunetti et al., *Biochimie* 83: 873, 2001; Zimmerman, *J Struct Biol* 153: 160, 2006) suggest that the primary role of H-NS is to silence foreign DNA. A degenerate recognition sequence and the ability to polymerize along and bridge adjacent stretches of DNA ideally suit H-NS for this role and likely account for many of its reported functions including alteration of recombination events and local supercoiling (Dorman, *Nat Rev Microbiol* 2: 391, 2004; Hardy and Cozzarelli, *Mol Microbiol* 57: 1636, 2005; Tupper et al., *Embo J* 13: 258, 1994).

The genome wide average GC content of various bacterial genera can vary from 25% to 75%, and attempts have been made to explain why bacterial genomes maintain their distinctive GC bias (Lee et al., *Appl Bioinformatics* 3: 219, 2004). The reason for the relative AT-richness of horizontally transferred DNA in enteric bacteria has also been enigmatic. The ability to discriminate self from foreign DNA on the basis of differences in GC-content can provide a fitness advantage and that xenogentic silencing has likely shaped bacterial genomes by facilitating the acquisition and preservation of AT-rich DNA. Interestingly some AT-rich bacteriophages, pathogenicity islands, and mobile genetic elements encode H-NS antagonists (Dorman, *Nat Rev Microbiol* 2: 391, 2004; Williamson and Free, *Mol Microbiol* 55: 808, 2005), indicating that "selfish" genetic elements have evolved countermechanisms to escape H-NS-mediated silencing.

Example 2

Silencing of Foreign DNA with Low GC Content by the H-NS Protein in *E. coli* hns mutations in two standard laboratory strains of *E. coli*, one of which expresses the commonly used phage T7 RNA polymerase were constructed. Four different AT-rich clones whose expression has proven to be difficult in standard strains of *E. coli* have been obtained.

Most commercially available plasmid vectors for protein expression use a promoter dependent on the T7 RNA polymerase. T7 RNA polymerase-dependent promoters are commonly used for protein expression because their activity can be tightly controlled, providing robust expression only when T7 polymerase is induced. T7 promoters are not recognized by the host RNA polymerases, which reduces unwanted background expression. These features make using T7 polymerase particularly useful when the protein of interest is toxic for *E. coli*. Other promoters frequently used for protein expression are derived from the lac (lactose) promoter, which is transcribed by the *E. coli* RNA polymerase. The lac-derived promoters are activated in the presence of lactose or lactose-analogues. Because of their widespread use and the fact that their biology is well understood, the expression studies will be carried on recombinant genes whose expression will be driven by the T7 or lac promoters.

Clones of two genes from *Plasmodium falciparum* (the malaria parasite), one clone from mouse and one from *Streptococcus*, have been obtained. These genes have been reported to be poorly expressed in *E. coli*. These clones are currently in commercially available plasmids and are under the control of the T7 promoter. Their expression will be tested in the wild-type and hns-mutant *E. coli* backgrounds by quantitative reverse-transcriptase PCR (Q-PCR—to measure RNA transcript levels) and by immunoblotting (to measure protein expression directly). By measuring both transcript and protein levels, it can be better understood at what steps H-NS interferes with protein expression. It is possible that H-NS can interfere with transcription within a gene (as well as during transcription initiation). To address this possibility, Q-PCR experiments will be designed to test RNA levels from both the start (5') and end (3') of each gene.

Clones encoding proteins currently under commercial production (caspase-1, G-CSF, insulin) will be obtained. The expression of these clones using experiments identical to those above will be determined.

It has been demonstrated that *E. coli* encodes a homologue to H-NS (StpA, encoded by stpA) that can partially compensate for mutations in hns. H-NS also acts in concert with at least two other proteins (YdgT and Hha) to silence gene expression at several promoters. It will be tested whether further improvements in protein expression can be achieved in strains deficient in these additional factors either alone or in combination with mutations in hns will be tested.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A method of expressing a foreign polypeptide in a host cell, the method comprising the steps of inhibiting the expression of at least one endogenous xenogeneic silencing protein, transferring a gene that encodes the foreign polypeptide into the host cell, wherein the gene consists of low GC content in comparison to the host cell genome, and culturing the host cell under conditions that allow expression of the foreign polypeptide, wherein the host cell is a non-quiescent hns mutant of *S. typhimurium, E. coli*, or *P. aeruginosa*, wherein the hns mutant has reduced activity of H-NS as compared to an otherwise isogenic cell.

2. The method of claim 1, wherein a mutation in the gene that encodes the xenogeneic silencing protein is introduced into the host cell.

3. The method of claim 2, wherein the mutation is a null mutation.

4. The method of claim 1, wherein the xenogeneic silencing protein is a DNA binding protein.

5. The method of claim 4, wherein the DNA binding protein is a H-NS protein or a H-NS homolog.

6. The method of claim 4, wherein the DNA binding protein is an StpA protein.

7. The method of claim 1, wherein the xenogeneic silencing protein is a protein that interacts with a DNA binding protein.

8. The method of claim 7, wherein the xenogeneic silencing protein is a Hha protein or a Hha homolog.

9. The method of claim 7, wherein the xenogeneic silencing protein is a YdgT protein.

10. The method of claim 4, wherein the xenogeneic silencing protein is a MvaT protein.

11. The method of claim 7, wherein the xenogeneic silencing protein is a MvaU protein.

12. The method of claim 1, further comprising the step of inhibiting the expression of an alternative sigma factor $\sigma^s$ protein.

13. The method of claim 12, wherein a mutation in the rpoS gene is introduced into the host cell.

14. The method of claim 1, further comprising the step of inhibiting the expression of an alternative sigma factor $\sigma^s$ dependent protein.

15. The method of claim 14, wherein the $\sigma^s$ dependent protein is CsgBA, HdeAB, Mcc (microcin C51), OsmY or a combination thereof.

16. The method of claim 1, wherein the host cell has an additional mutation in the rpoS genes.

17. The method of claim 1, further comprising the step of inhibiting the expression of the virulence gene regulator protein, PhoP.

18. The method of claim 17, wherein a mutation in the phoP gene is introduced into the host cell.

19. The method of claim 16, wherein the host cell has an additional mutation in the phoP gene.

20. The method of claim 1, wherein the polypeptide is caspase-1, G-CSF, or insulin.

21. A method of expressing a foreign polypeptide in a non-quiescent bacterial host cell, the method comprising the steps of introducing a recombinant expression cassette comprising a nucleic acid sequence that encodes the foreign polypeptide for expression into the host cell, wherein the nucleic acid sequence consists of low GC content in comparison to the host cell genome; inhibiting the expression of at least one endogenous xenogeneic silencing protein; and culturing the host cell under conditions that allow expression of the foreign polypeptide, wherein the host cell is a hns mutant of *S. typhimurium, E. coli*, or *P. aeruginosa*, wherein the hns mutant has reduced activity of H-NS as compared to an otherwise isogenic cell.

22. A non-quiescent host cell for expressing a foreign polypeptide comprising a recombinant expression cassette comprising a nucleic acid sequence that encodes the foreign polypeptide for expression, wherein the nucleic acid sequence consists of low GC content in comparison to the host cell genome; wherein the host cell has decreased expression of an endogenous xenogeneic silencing protein, and wherein the host cell is a hns mutant of *S. typhimurium, E. coli*, or *P. aeruginosa*, wherein the hns mutant has reduced activity of H-NS as compared to an otherwise isogenic cell.

23. The method of claim 4, wherein the DNA binding protein is at least 70% homologous to SEQ ID NO: 1.

24. The method of claim 4, wherein the DNA binding protein is at least 70% homologous to H-NS protein.

25. A method of expressing an exogenous polypeptide in a bacterial host cell, comprising introducing a gene that encodes the exogenous polypeptide into the host cell and culturing the host cell under conditions that allow expression of the exogenous polypeptide;

wherein the gene encoding the exogenous polypeptide has GC content lower than the average GC content of the host cell genome;

wherein the host cell is a *S.typhimurium, E. coli*, or *P. aeruginosa* cell with reduced expression or activity of H-NS as compared to an otherwise isogenic cell.

26. The method of claim 25, wherein the reduced expression is caused by a mutation in the hns gene.

27. The method of claim 26, wherein the mutation in the hns genes is introduced into the host cell.

28. The method of claim 26, wherein the mutation is a null mutation.

* * * * *

SEQUENCE LISTING

```
<160> NUMBER OF SEQ ID NOS: 24

<210> SEQ ID NO 1
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Gly or Ser
<220> FEATURE:
<221> NAME/KEY: MISC_FEATURE
<222> LOCATION: (9)..(9)
<223> OTHER INFORMATION: Xaa can be Glu or Asp
<220> FEATURE:
<221> NAME/KEY: MISC_FEATURE
<222> LOCATION: (10)..(11)
<223> OTHER INFORMATION: Xaa can be any naturally occurring amino acid;
      neither or both may be absent
<220> FEATURE:
<221> NAME/KEY: MISC_FEATURE
<222> LOCATION: (14)..(14)
<223> OTHER INFORMATION: Xaa can be Thr or Ser
<220> FEATURE:
<221> NAME/KEY: MISC_FEATURE
<222> LOCATION: (16)..(16)
<223> OTHER INFORMATION: Xaa can be Gln or Arg
<220> FEATURE:
<221> NAME/KEY: MISC_FEATURE
<222> LOCATION: (18)..(18)
<223> OTHER INFORMATION: Xaa can be Arg or Lys
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (21)..(25)
<223> OTHER INFORMATION: Xaa can be any naturally occurring amino acid;
      one may be absent
<220> FEATURE:
<221> NAME/KEY: MISC_FEATURE
<222> LOCATION: (27)..(30)
<223> OTHER INFORMATION: Xaa can be any naturally occurring amino acid;
      one may be absent

<400> SEQUENCE: 1

Tyr Xaa Xaa Xaa Xaa Xaa Xaa Xaa Xaa Xaa Xaa Thr Trp Xaa Gly Xaa
1               5                   10                  15

Gly Xaa Xaa Pro Xaa Xaa Xaa Xaa Xaa Ala Xaa Xaa Xaa Xaa Gly
```

<210> SEQ ID NO 2
<211> LENGTH: 5
<212> TYPE: PRT
<213> ORGANISM: Artificial Sequence
<220> FEATURE:
<223> OTHER INFORMATION: Synthetic construct

<400> SEQUENCE: 2

Tyr Leu Gly Glu Ile
1               5

<210> SEQ ID NO 3
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 3
gagataatta aaacgtgtgc ttaataaagc gtaattttga gtgtaggctg gagctgcttc      60

<210> SEQ ID NO 4
<211> LENGTH: 60
<212> TYPE: DNA
<213> ORGANISM: Artificial Sequence
<220> FEATURE:
<223> OTHER INFORMATION: Oligonucleotide primer

<400> SEQUENCE: 4
acatagctat atttagccgg acgagctgcg cgtttagctt catatgaata tcctccttag      60

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 5
ttggatccga cgacaaaccg atacgagag                                        29

<210> SEQ ID NO 6
<211> LENGTH: 49
<212> TYPE: DNA
<213> ORGANISM: Artificial Sequence
<220> FEATURE:
<223> OTHER INFORMATION: Oligonucleotide primer

<400> SEQUENCE: 6
ttattaaagc ttggctgcag attccttgat caggaaatct tccagttgc                  49

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Ala Asp Tyr Lys Asp Asp Asp Asp Lys
1               5

<210> SEQ ID NO 8
<211> LENGTH: 11
<212> TYPE: PRT

-continued

```
<213> ORGANISM: Artificial Sequence
<220> FEATURE:
<223> OTHER INFORMATION: Synthetic construct

<400> SEQUENCE: 8

Ala Asp Tyr Pro Tyr Asp Val Pro Asp Tyr Ala
1               5                   10

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 9
aaaggatccc cgaaaagtgc cacctg                                          26

<210> SEQ ID NO 10
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 10
aaaggatccg caagatccgc agttcaacc                                       29

<210> SEQ ID NO 11
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 11
tatagatctc caacctggag tctttccgta tg                                   32

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 12
tatagatctc attttatcg ccgccactg                                        29

<210> SEQ ID NO 13
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 13
aaggatccta cacaatcgct caagac                                          26

<210> SEQ ID NO 14
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 14
aaaggatccc gggaattcgt gtaggctgga gctgcttc                             38
```

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 15
taaaggtgta gcacaccacc acca                                          24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
tttgagagaa ggctcatttg ccgc                                          24

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 17
tcaggtggat ttttgctggt tg                                            22

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 18
tattgcgagg tgctatcggc tgtg                                          24

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 19
ttgaacgtcc gggtcaatgt ttgc                                          24

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 20
tattccaaat ggcacctgca acgg                                          24

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide primer

```
<400> SEQUENCE: 21
gatgggtttt ccagcaggta ttc                                           23

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 22
aggtctgatt gcggtggttt c                                             21

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 23
tgcaggaaga acagcgtaac cgta                                          24

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 24
tcggcgtaat acctttcgcc atct                                          24
```